(12) United States Patent
Zacharie et al.

(10) Patent No.: US 9,475,750 B2
(45) Date of Patent: *Oct. 25, 2016

(54) PHENYLKETONE CARBOXYLATE COMPOUNDS AND PHARMACEUTICAL USES THEREOF

(75) Inventors: Boulos Zacharie, Laval (CA); Christopher Penney, Pierrefonds (CA); Shaun Abbott, Pointe-Claire (CA); Lyne Gagnon, Laval (CA); Brigitte Grouix, Montreal (CA); Pierre Laurin, Ville Mont-Royal (CA); Jean-François Bienvenu, Quebec (CA)

(73) Assignee: PROMETIC BIOSCIENCES INC., Laval, Quebec (CA)

( * ) Notice: Subject to any disclaimer, the term of this patent is extended or adjusted under 35 U.S.C. 154(b) by 416 days.

This patent is subject to a terminal disclaimer.

(21) Appl. No.: 13/882,363

(22) PCT Filed: Oct. 26, 2011

(86) PCT No.: PCT/CA2011/001176
§ 371 (c)(1),
(2), (4) Date: May 21, 2014

(87) PCT Pub. No.: WO2012/055014
PCT Pub. Date: May 3, 2012

(65) Prior Publication Data
US 2013/0225681 A1    Aug. 29, 2013

Related U.S. Application Data

(60) Provisional application No. 61/407,068, filed on Oct. 27, 2010.

(51) Int. Cl.
| | |
|---|---|
| C07C 59/90 | (2006.01) |
| C07C 62/38 | (2006.01) |
| C07C 65/32 | (2006.01) |
| C07C 69/92 | (2006.01) |
| C07C 217/84 | (2006.01) |
| C07C 225/22 | (2006.01) |
| C07C 229/18 | (2006.01) |
| C07C 323/20 | (2006.01) |
| C07C 323/52 | (2006.01) |
| C07C 323/62 | (2006.01) |
| A61K 31/192 | (2006.01) |
| A61K 31/196 | (2006.01) |
| A61K 31/222 | (2006.01) |
| A61K 31/235 | (2006.01) |
| C07C 59/68 | (2006.01) |
| C07C 59/84 | (2006.01) |

(52) U.S. Cl.
CPC ............ C07C 59/90 (2013.01); A61K 31/192 (2013.01); A61K 31/196 (2013.01); A61K 31/222 (2013.01); A61K 31/235 (2013.01); C07C 59/68 (2013.01); C07C 59/84 (2013.01); C07C 62/38 (2013.01); C07C 65/32 (2013.01); C07C 69/92 (2013.01); C07C 217/84 (2013.01); C07C 225/22 (2013.01); C07C 229/18 (2013.01); C07C 323/20 (2013.01); C07C 323/52 (2013.01); C07C 323/62 (2013.01); C07C 2102/08 (2013.01)

(58) Field of Classification Search
CPC ............ A61K 31/192; A61K 31/196; A61K 31/222; A61K 31/235; C07C 2102/08; C07C 217/84; C07C 225/22; C07C 229/18; C07C 323/20; C07C 323/52; C07C 323/62; C07C 59/68; C07C 59/84; C07C 59/90; C07C 62/38; C07C 65/32; C07C 69/92
See application file for complete search history.

(56) References Cited

U.S. PATENT DOCUMENTS 3,870,752 A * 3/1975 Houlihan et al. .............. 562/462
3,907,792 A * 9/1975 Mieville ............... C07C 51/347
                                                          540/544

FOREIGN PATENT DOCUMENTS

| ES | 2 050 072 | 5/1994 |
| GB | 1 415 295 | 11/1975 |
| WO | WO 2005/021481 A1 | 3/2005 |

OTHER PUBLICATIONS

Aono et. al., Chemical and Pharmaceutical Bulletin, 1977, Pharmaceutical Society of Japan, vol. 25(12), pp. 3198-3209.*
Ainsworth, C. et al., "Cholesterol-Solubilizing Agents Related to the Gallstone Problem," *Journal of Medical Chemistry*, Mar. 1967, vol. 10, No. 2, p. 158-161.

* cited by examiner

*Primary Examiner* — Sarah Pihonak
(74) *Attorney, Agent, or Firm* — Saliwanchik, Lloyd & Eisenschenk

(57) ABSTRACT

Phenylketone carboxylate compounds of Formula I, wherein n=2-6; R=C(0); —OC(O)— or —CH(OH)—; A is (CH2) mCOOH, W(CH2)mCOOH or YCH(COOH)((CH2)pCH3) when B is Ft B is (CH2)mCOOH, W(CH2)mCOOH or YCH(COOH)((CH2)pCH3) when A is Ft or A and B form a 5-7 membered cycloalkyl substituted with COOFt W=0, S or NFt Y=0,S,NH or CH2; m=0-2; p=1-7; have been prepared. These compounds and their pharmaceutically acceptable salts have beneficial therapeutic effects to prevent or treat a condition related to (l) blood disorders, (ii) inflammation related diseases, (iii) renal disorders and/or renal disorders complications, or (iv) fibrosis-related organ dysfunction.

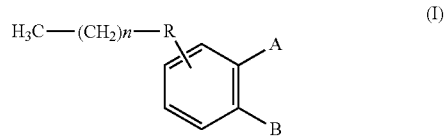

(I)

24 Claims, 11 Drawing Sheets

CY = Cyclophosphamide

NX = nephrectomized rats

PHENYLKETONE CARBOXYLATE COMPOUNDS AND PHARMACEUTICAL USES THEREOF

CROSS REFERENCE TO A RELATED APPLICATION

This application is a National Stage Application of International Application Number PCT/CA2011/001176, filed Oct. 26, 2011; which claims priority to U.S. Provisional Application No. 61/407,068, filed Oct. 27, 2010; which are incorporated herein by reference in their entirety.

FIELD OF INVENTION

The present invention relates to phenylketone carboxylate compounds and their pharmaceutical uses. More particularly, the invention relates to pharmaceutical compositions comprising the same and to their use for the prevention or treatment of various diseases and conditions arising from anemia, neutropenia, leukopenia, inflammation and/or fibrosis in subjects.

BACKGROUND OF INVENTION

Blood Disorders

Hematopoiesis (hema=blood) refers to the process of formation, development and differentiation of all types of blood cells. All cellular blood components are derived from hematopoietic stem cells, including leukocytes and erythrocytes. The leukocytes or white blood cells (WBCs) contains the cells of the immune system defending the body against infectious disease and foreign materials. The erythrocytes are the non-nucleated, biconcave, disk-like cells which contain hemoglobin and these cells are essential for the transport of oxygen. A reduction in the number of white blood cells is called leukopenia whereas anemia refers to that condition which exists when there is a reduction below normal in the number of erythrocytes, the quantity of hemoglobin, or the volume of packed red blood cells in the blood. Disorders of the blood and the several kinds of leukopenia and anemia may be produced by a variety of underlying causes, including chemotherapy (e.g., chemotherapy induced anemia) and cancers (e.g., cancer related anemia). Therefore, there is a need for novel compositions and methods to stimulate hematopoiesis and to address the undesirable side effects of myelosuppression induced by chemotherapy and radiation therapy.

Inflammation

Immune Mediated Inflammatory Disease (IMID) refers to any of a group of conditions or diseases that lack a definitive etiology but which are characterized by common inflammatory pathways leading to inflammation, and which may result from, or be triggered by, a dysregulation of the normal immune response. Autoimmune disease refers to any of a group of diseases or disorders in which tissue injury is associated with a humoral and/or cell-mediated immune response to body constituents or, in a broader sense, an immune response to self. Current treatments for autoimmune disease can be broadly classified into two groups: those drugs which dampen or suppress the immune response to self and those drugs which address the symptoms that arise from chronic inflammation. In greater detail, conventional treatments for autoimmune diseases (e.g., primarily arthritis) are (1) Nonsteroidal Anti-Inflammatory Drugs (NSAIDs) such as aspirin, ibuprofen, naproxen, etodolac, and ketoprofen; (2) Corticosteroids such as prednisone and dexamethasone; (3) Disease-Modifying Anti-Rheumatic Drugs (DMARDs) such as methotrexate, azathioprine, cyclophosphamide, cyclosporin A, Sandimmune™ Neoral™, and FK506 (tacrolimus); (4) Biologicals such as the recombinant proteins Remicade™ Enbrel™ and Humira™. While numerous therapies are available, conventional treatments are not routinely efficacious. More problematic is the accompanying toxicity which often prohibits the long-term use necessary with a chronic disease. Therefore, there is a need for compounds that are useful for the treatment of inflammation-related diseases, including chronic and non-chronic autoimmune disease.

Fibrosis and Kidney Disease

Fibrosis refers to the formation or development of excess fibrous connective tissue in an organ or tissue that can occur as a part of the wound-healing process in damaged tissue. It may be viewed as an exaggerated form of wound healing that does not resolve itself.

Fibrosis can occur on the skin but it can also occur in internal organs such as the kidney, heart, lung, liver and brain. In the case of organs, fibrosis will often precede sclerosis and subsequent shutdown of the affected organ. Of course, the most common consequence of complete organ failure is death. Thus, for example, pulmonary fibrosis is a major cause of morbidity and mortality. It is associated with the use of high dose chemotherapy (e.g., bleomycin) and bone marrow transplantation. Idiopathic pulmonary fibrosis (IPF) is a lung fibrotic disease for which the median survival is four to five years after the onset of symptoms. Currently there are no effective antifibrotic drugs approved for human needs. Therefore, the need exists for compounds that are useful for the treatment of fibrotic diseases.

Renal fibrosis is the common pathway underlying the progression of chronic renal injury to end-stage renal disease. The kidney is a structurally complex organ that performs a number of important functions: excretion of the waste products of metabolism, regulation of body water and salt, maintenance of acid balance, and excretion of a variety of hormones and autocoids. Diseases of the kidney are complex but their study is facilitated by dividing them by their effects on four basic morphologic components: glomeruli, tubules, interstitium, and blood vessels. Unfortunately, some disorders affect more than one structure and the anatomic interdependence of structures in the kidney implies that damage to one almost always secondarily affects the others. Thus, whatever the origin, there is a tendency for all forms of renal disease ultimately to destroy all four components of the kidney, culminating in chronic renal failure. For instance, in autoimmune diseases such as diabetes mellitus, the kidneys are prime targets to suffer tissue damage or lesions. Nephrectomy, or kidney removal, a procedure which is sometimes performed on patients with kidney cancer (e.g., renal cell carcinoma), may negatively impact kidney function in the remaining kidney. Chemotherapy and immunosuppressive therapy are also a source of harmful effects to the kidneys. Therefore, there exists a need for drugs with a good safety profile which can be administered to patients with kidney disease. There is also a need for pharmaceutical compounds which can prolong kidney health or protect it from deterioration to the point at which the kidney can no longer function.

The present invention addresses these needs for new treatment methods, compounds and pharmaceutical compositions. The invention provides new chemical entities and new treatment methods for preventing and/or treating (i) blood disorders, (ii) inflammation-related diseases and/or (iii) renal disorders and/or renal disorder complications along with any other organ dysfunction or lesion(s) arising from fibrotic disease.

Additional features of the invention will be apparent from a review of the disclosure, figures and description of the invention herein.

BRIEF SUMMARY OF THE INVENTION

The present invention relates to compounds, compositions and methods for the prevention and/or treatment of various diseases and conditions in subjects.

Particular aspects of the invention relate to compounds according to Formula I and Formula II as defined herein and pharmaceutically acceptable salts thereof. Other aspects of the invention relates to the use of compounds according to Formula I and Formula II as defined herein and pharmaceutically acceptable salts thereof.

One particular aspect of the invention concerns the use of a compound represented by Formula I or Formula II as defined herein for prevention and/or treatment of (i) blood disorders (e.g., anemia, neutropenia), (ii) inflammation-related diseases (e.g., autoimmune disease), (iii) renal disorders and/or renal disorder complications and/or (iv) fibrosis-related organ dysfunctions. Another particular aspect of the invention concerns the use of a compound represented by Formula I or Formula II as defined herein for prevention and/or treatment of a condition associated with: (i) blood disorders (e.g., anemia, neutropenia), (ii) inflammation-related diseases (e.g., autoimmune disease), (iii) renal disorders and/or renal disorder complications and/or (iv) fibrosis-related organ dysfunctions.

Another related aspect of the invention relates to a pharmaceutical composition comprising a compound of Formula I or Formula II as defined herein for use in prevention or treatment of (i) blood disorders (e.g., anemia, neutropenia), (ii) inflammation-related diseases (e.g., autoimmune disease), (iii) renal disorders and/or renal disorder complications and/or (iv) fibrosis-related organ dysfunctions. Yet another related aspect of the invention relates to a pharmaceutical composition comprising a compound of Formula I or Formula II as defined herein for the manufacture of a medicament for the prevention or treatment of: (i) blood disorders (e.g., anemia, neutropenia), (ii) inflammation-related diseases (e.g., autoimmune disease), (iii) renal disorders and/or renal disorder complications and/or (iv) fibrosis-related organ dysfunctions. One particular example is a nephroprotective composition comprising a compound represented by Formula I or Formula II as defined herein, and a pharmaceutically acceptable carrier.

A related aspect of the invention relates to a method for the prevention or treatment of (i) blood disorders (e.g., anemia, neutropenia), (ii) inflammation-related diseases (e.g., autoimmune disease), (iii) renal disorders and/or renal disorder complications and/or (iv) fibrosis-related organ dysfunctions, comprising administering to a subject in need thereof a therapeutically effective amount of a Compound of Formula I or Formula II as defined herein or a pharmaceutical composition comprising a Compound of Formula I or Formula II as defined herein and pharmaceutical acceptable vehicle.

The invention further relates to compounds according to Formula I or Formula II as defined herein, and pharmaceutically acceptable salts thereof, as prophylactically effective and/or therapeutically effective agents against various diseases and/or conditions in subjects.

Further aspects of the invention will be apparent to a person skilled in the art from the following description, claims, and generalizations herein.

DETAILED DESCRIPTION OF THE INVENTION

A) General Overview of the Invention

Figure 1:
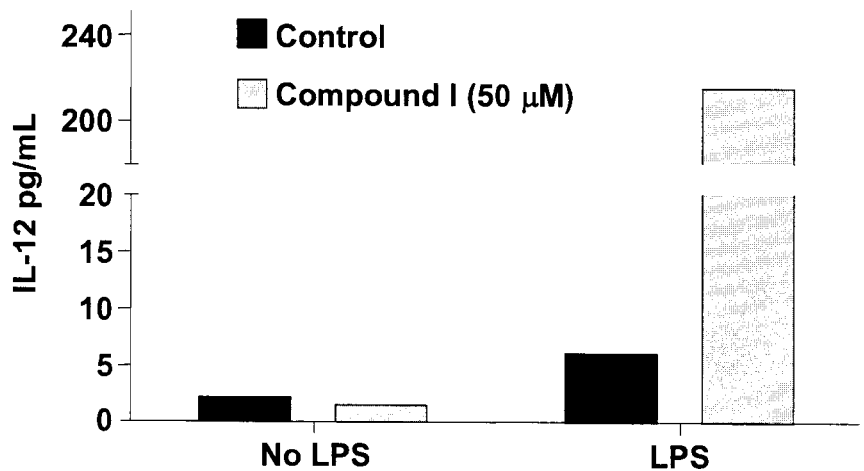
FIG. 1 is a bar graph showing the effects of Compound I on IL-12 production in vitro (RAW.264 cells) under non-inflammatory and inflammatory conditions.

The present invention discloses compounds of Formula I and Formula II that have beneficial pharmaceutical properties. For instance, the compounds according to the invention may be effective for stimulating the production of red and/or white blood cells in anemic and/or neutropenic individuals, in individuals with inflammatory diseases, and/or individuals who require kidney protection which may include treatment of high blood pressure and/or protection of other organs (heart, liver, lungs, brain) that are subject to fibrotic disease.

B) Compounds of the Invention

According to one aspect, the invention concerns novel compounds represented by Formula I, or a pharmaceutically acceptable salt thereof:

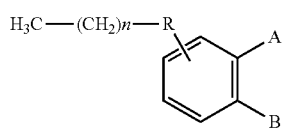

I wherein:
n is 2-6;
R is —C(O)—, —OC(O)—, —CH(OH)—, NH, NR', O, S, or $CH_2$;
A is $(CH_2)_m COOH$, $W(CH_2)_m COOH$ or

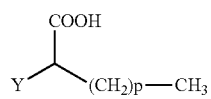

when B is H;
B is $(CH_2)_m COOH$, $W(CH_2)_m COOH$ or

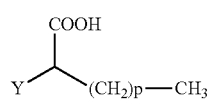

when A is H; or
A and B are covalently bonded to form a five (5), six (6) or seven (7)-membered cycloalkyl substituted with COOH;
where:
R' is a $C_{1-3}$ alkyl;
W is O, S, or NH;
Y is O, S, NH, or $CH_2$;
m is 0-2; and
p is 1-7.

In a preferred embodiment, R is —C(O)—, —OC(O)—, or —CH(OH)—. In a further preferred embodiment, R is —C(O)—.

In a preferred embodiment, p is 3-7.

According to another aspect, the invention concerns novel compounds represented by Formula II, or a pharmaceutically acceptable salt thereof:

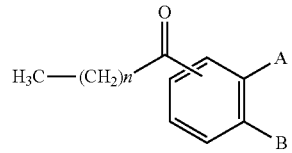

II wherein:
n is 2-6;
A is $(CH_2)_m COOH$, $W(CH_2)_m COOH$ or

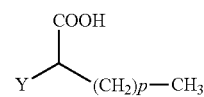

when B is H;
B is $(CH_2)_m COOH$, $W(CH_2)_m COOH$ or

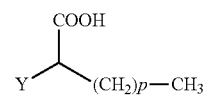

when A is H; or
A and B are covalently bonded to form a five (5), six (6) or seven (7)-membered cycloalkyl substituted with COOH;
where:
Y is O, S, NH, or $CH_2$;
W is O, S, or NH;
m is 0-2; and
p is 3-7.

According to another aspect, the invention concerns particular medical and pharmaceutical uses and methods for prevention or treatment of a subject with compounds represented Formula I, or a pharmaceutically acceptable salt thereof:

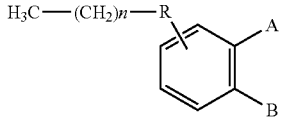

I wherein:
n is 2-6;
R is —C(O)—, —OC(O)—, —CH(OH)—, NH, NR', O, S, or CH$_2$;
A is (CH$_2$)$_m$COOH, W(CH$_2$)$_m$COOH or

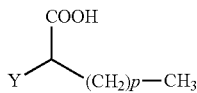

when B is H;
B is (CH$_2$)$_m$COOH, W(CH$_2$)$_m$COOH or

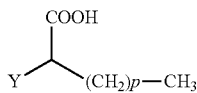

when A is H; or
A and B are covalently bonded to form a five (5), six (6) or seven (7)-membered cycloalkyl substituted with COOH;
where:
R' is a C$_{1-3}$ alkyl;
W is O, S, or NH;
Y is O, S, NH, or CH$_2$;
m is 0-2; and
p is 1-7.

In a further aspect, the invention concerns particular medical and pharmaceutical uses and methods for prevention or treatment of a subject with compounds represented Formula I, or a pharmaceutically acceptable salt thereof of the invention, where R is —C(O)—, —OC(O)—, or —CH(OH)—. In a preferred embodiment of such uses and methods, p is 3-7.

According to another further aspect, the invention concerns particular medical and pharmaceutical uses and methods for prevention or treatment of a subject with compounds represented by Formula II, or a pharmaceutically acceptable salt thereof:

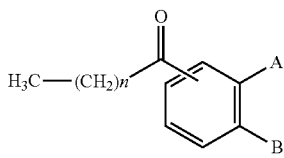

II wherein:
n is 2-6;
A is (CH$_2$)$_m$COOH, W(CH$_2$)$_m$COOH or

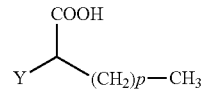

when B is H;
B is (CH$_2$)$_m$COOH, W(CH$_2$)$_m$COOH or

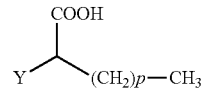

when A is H; or
A and B are covalently bonded to form a five (5), six (6) or seven (7)-membered cycloalkyl substituted with COOH;
where:
Y is O, S, NH, or CH$_2$;
W is O, S, or NH;
m is 0-2; and
p is 3-7.

As used herein, the term "cycloalkyl" is intended to mean a monocyclic saturated aliphatic hydrocarbon group having the specified number of carbon atoms therein, for example, as in C$_5$-C$_7$ cycloalkyl is defined as including groups having 5, 6 or 7 carbons in a monocyclic arrangement. Examples of C$_5$-C$_7$ cycloalkyl include, but are not limited to, cyclopentyl, cyclohexyl and cycloheptyl.

As used herein, the term "alkyl" is intended to include a straight chain saturated aliphatic hydrocarbon group having the specified number of carbon atoms, for example, C$_1$-C$_3$ as in C$_1$-C$_3$ alkyl is defined as including groups having 1, 2, or 3 carbons in a linear arrangement. Examples of alkyl defined above include, but are not limited to, methyl, ethyl and n-propyl.

Examples of compounds of Formula I and Formula II include but are not limited to, the compounds listed in Table 1 hereinafter.

In embodiments of the invention, the pharmaceutically acceptable salt of the compounds of Formula I or Formula II are base addition salts of sodium, potassium, calcium, magnesium or lithium. In a preferred embodiment, the compound is a sodium salt. In some embodiments, the compounds are the sodium salts listed in Table 1 hereinafter. More preferably, the compound is Compound I, II, III, X or XXII as defined herein.

TABLE 1

Examples of compounds of Formula I and Formula II

Compound No. Structure

I 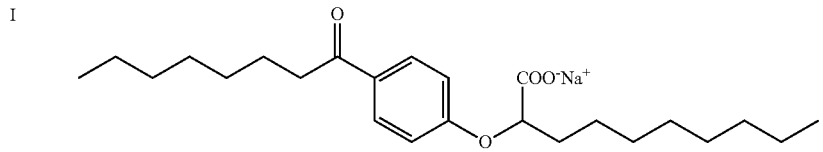

TABLE 1-continued
Examples of compounds of Formula I and Formula II
Compound No. Structure
II 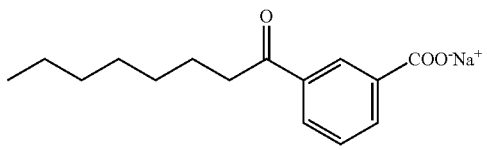
III 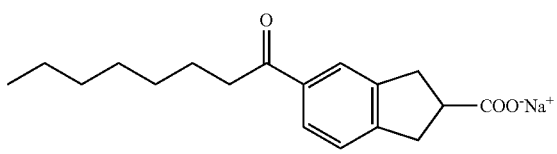
IV 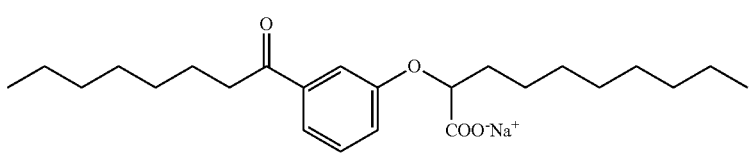
V 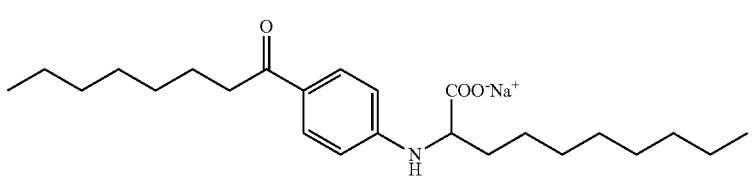
VI 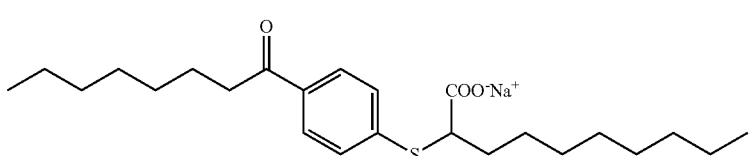
VII 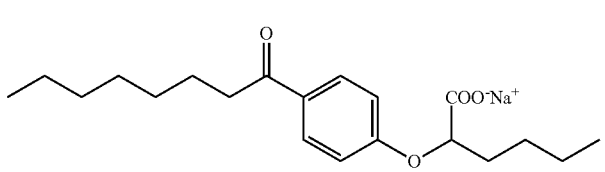
VIII 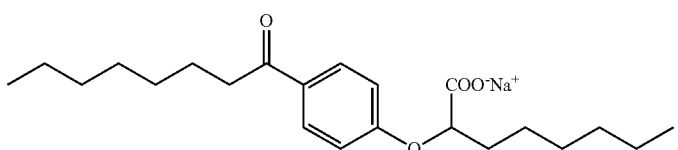
IX 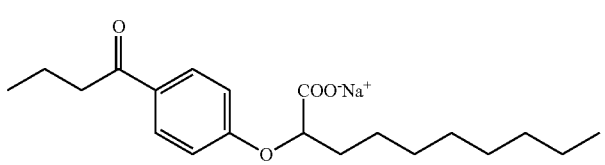
X 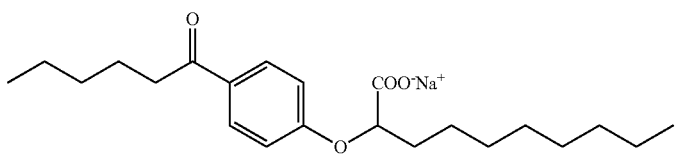

TABLE 1-continued
Examples of compounds of Formula I and Formula II
Compound No. Structure
XI 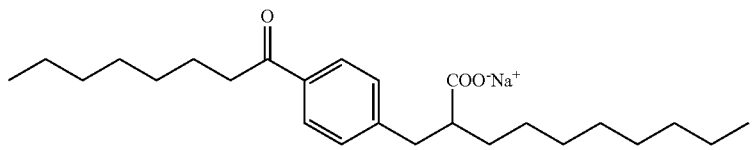
XII 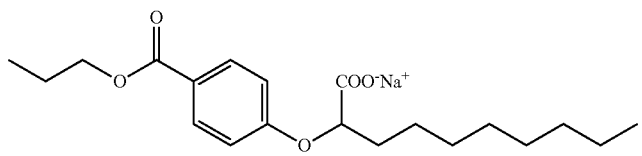
XIII 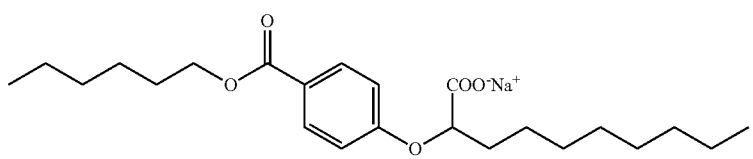
XIV 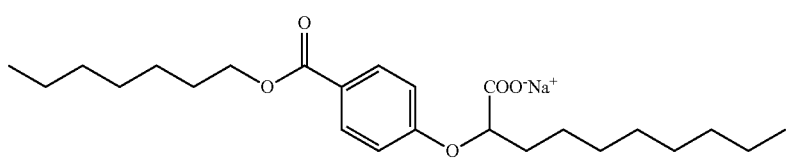
XV 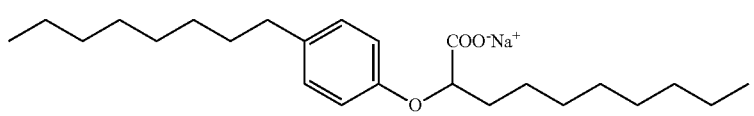
XVI 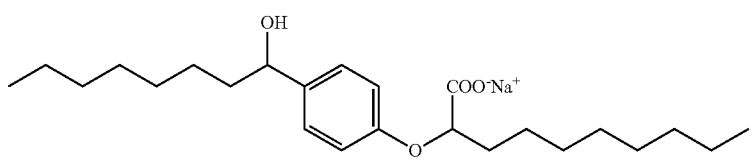
XVII 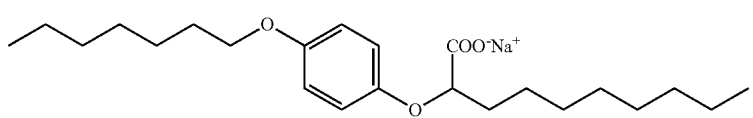
XVIII 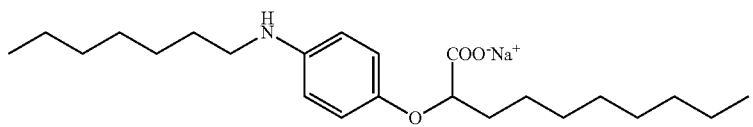
XIX 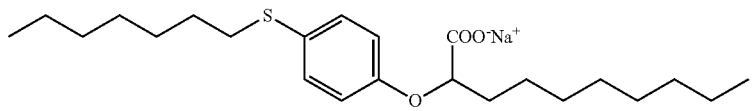
XX 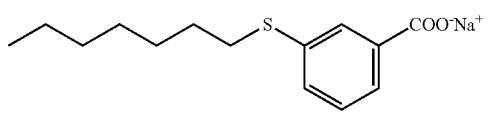

TABLE 1-continued

Examples of compounds of Formula I and Formula II

| Compound No. | Structure |
|---|---|
| XXI | (hexyl-C(=O)-phenyl-4-O-CH2-COO⁻Na⁺) |
| XXII | (hexyl-C(=O)-phenyl-3-O-CH2-COO⁻Na⁺) |
| XXIII | (hexyl-NH-phenyl-3-COO⁻Na⁺) |
| XXIV | (heptyl-phenyl-3-COO⁻Na⁺) |
| XXV | (hexyl-O-phenyl-3-COO⁻Na⁺) |
| XXVI | (hexyl-C(=O)-(2,3-dihydro-1H-indene-2-COO⁻Na⁺)) |

The compounds of the present invention, or their pharmaceutically acceptable salts may contain one or more asymmetric centers, chiral axes and chiral planes and may thus give rise to enantiomers, diastereomers, and other stereoisomeric forms and may be defined in terms of absolute stereochemistry, such as (R)- or (S)- or, as (D)- or (L)-. The present invention is intended to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. The racemic mixtures may be prepared and thereafter separated into individual optical isomers or these optical isomers may be prepared by chiral synthesis. The enantiomers may be resolved by methods known to those skilled in the art, for example by formation of diastereoisomeric salts which may then be separated by crystallization, gas-liquid or liquid chromatography, selective reaction of one enantiomer with an enantiomer specific reagent. It will also be appreciated by those skilled in the art that where the desired enantiomer is converted into another chemical entity by a separation technique, an additional step is then required to form the desired enantiomeric form. Alternatively specific enantiomers may be synthesized by asymmetric synthesis using optically active reagents, substrates, catalysts, or solvents or by converting one enantiomer to another by asymmetric transformation.

Certain compounds of the present invention may exist in Zwitterionic form and the present invention includes Zwitterionic forms of these compounds and mixtures thereof.

Salts

As used herein, the term "pharmaceutically acceptable salt" is intended to mean base addition salts. Example of pharmaceutically acceptable salts are also described, for example, in Berge et al., "Pharmaceutical Salts", *J. Pharm. Sci.* 66, 1-19 (1977). Pharmaceutically acceptable salts may be synthesized from the parent agent that contains an acidic moiety, by conventional chemical methods. Generally, such salts are prepared by reacting the free acid forms of these agents with a stoichiometric amount of the appropriate base in water or in an organic solvent, or in a mixture of the two. Salts may be prepared in situ, during the final isolation or purification of the agent or by separately reacting a purified compound of the invention in its free acid form with the desired corresponding base, and isolating the salt thus formed.

All acid, salt and other ionic and non-ionic forms of the compounds described are included as compounds of the invention. For example, if a compound is shown as an acid herein, the salt forms of the compound are also included. Likewise, if a compound is shown as a salt, the acid forms are also included.

Prodrugs

In certain embodiments, the compounds of the present invention as represented by generalized Formula I or Formula II, wherein these compounds are present in the free carboxylic acid form, may also include all pharmaceutically acceptable salts, isosteric equivalents such as tetrazole and prodrug forms thereof. Examples of the latter include the pharmaceutically acceptable esters or amides obtained upon reaction of alcohols or amines, including amino acids, with the free acids defined by Formula I or Formula II.

Hydrates

In addition, the compounds of the invention also may exist in hydrated and anhydrous forms. Hydrates of any of the formulas described herein are included as compounds of the invention which may exist as a monohydrate or in the form of a polyhydrate.

C) Methods of Preparation

In general, all compounds of the present invention may be prepared by any conventional methods, using readily available and/or conventionally preparable starting materials, reagents and conventional synthesis procedures. Of particular interest is the work of Hundertmark, T.; Littke, A. F.; Buchwald, S. L.; Fu, G. C. *Org. Lett.* 2000, 12, pp. 1729-1731.

The exemplification section hereinafter provides specific, but non limitative, examples for the synthesis of Compounds I, II, III, X or XXII.

D) Pharmaceutical Applications

As indicated and exemplified herein, the compounds of the present invention have beneficial pharmaceutical properties and these compounds may have useful pharmaceutical applications in the prevention and/or treatment of various diseases and/or conditions in a subject. Medical and pharmaceutical applications contemplated by the inventors include, but are not limited to, those which address blood disorders, inflammation-related diseases, and renal disorders and subsequent renal failure or other organ dysfunction or lesion(s) arising from fibrotic disease.

The term "subject" includes living organisms in which blood disorders, inflammation-related diseases, and renal failure or other organ dysfunction or lesion(s) arising from fibrotic disease can occur, or which are susceptible to such conditions. The term "subject" includes animals such as mammals or birds. Preferably, the subject is a mammal. More preferably, the subject is a human. Most preferably, the subject is a human patient in need of treatment.

As used herein, "preventing" or "prevention" is intended to refer to at least the reduction of likelihood of the risk of (or susceptibility to) acquiring a disease or disorder (i.e., causing at least one of the clinical symptoms of the disease not to develop in a patient that may be exposed to or predisposed to the disease but does not yet experience or display symptoms of the disease). Biological and physiological parameters for identifying such patients are provided herein and are also well known by physicians.

The terms "treatment" or "treating" of a subject includes the application or administration of a compound of the invention to a subject (or application or administration of a compound of the invention to a cell or tissue from a subject) with the purpose of delaying, stabilizing, curing, healing, alleviating, relieving, altering, remedying, less worsening, ameliorating, improving, or affecting the disease or condition, the symptom of the disease or condition, or the risk of (or susceptibility to) the disease or condition. The term "treating" refers to any indication of success in the treatment or amelioration of an injury, pathology or condition, including any objective or subjective parameter such as abatement; remission; lessening of the rate of worsening; lessening severity of the disease; stabilization, diminishing of symptoms or making the injury, pathology or condition more tolerable to the subject; slowing in the rate of degeneration or decline; making the final point of degeneration less debilitating; or improving a subject's physical or mental well-being. In some embodiments, the term "treating" can include increasing a subject's life expectancy and/or delay before additional treatments are required (e.g., dialysis or kidney transplantation).

Blood Disorders and Hematopoiesis

Addressing blood disorders is among the medical and pharmaceutical applications contemplated by present invention. The term "blood disorder" refers to any alteration in normal physiology, formation, proliferation and/or function of erythrocytes, leukocytes and/or platelets. Therefore, in one of its aspects the present invention relates to methods, compounds and compositions for stimulating hematopoiesis, and/or increasing blood cell count of erythrocytes (red blood cells), leukocytes (white blood cells) and/or platelets, in a subject, preferably a human patient in need thereof.

Accordingly, one aspect of the invention relates to the use of the compounds described herein for stimulating production of leukocytes in a subject in need thereof and/or for inhibiting decrease of leukocytes (i.e., leukopenia or leukocytopenia) in a subject. Related aspects include use of these compounds for stimulating a subject's immune system and reduce a subject's risk for infection. In one embodiment, the leukocytes are neutrophil granulocytes and the disorder is neutropenia. As is known, low white cell counts are often associated with chemotherapy, radiation therapy, leukemia, myelofibrosis and aplastic anemia. In addition, many common medications can cause leukopenia (e.g., minocyclen, a commonly prescribed antibiotic). Accordingly, the invention also relates to the use of the compounds described herein for the prevention and/or treatment of those particular diseases and conditions.

In order to evaluate, assess, and/or confirm the efficacy of the method, compounds and/or compositions of the invention, serial measurements can be determined. Quantitative assessment of blood cell count, hematopoiesis and erythropoiesis are well known in the art.

Typically a normal total white blood cell count in humans is within the range of 4,300 to 10,000 per $mm^3$ (or mL), with an average value taken as 7,000 per $mm^3$. A normal neutrophil count in human blood is within the range of 1,800 to 7,200 per $mm^3$. Therefore, leukopenia refers to the condition wherein the blood white cell or leukocyte count is reduced to 5,000 per $mm^3$ or less. In some embodiments, the subject is a human patient having a total white blood cells count under about 8,000 per $mm^3$, or under about 5,000 per $mm^3$ or under about 4,000 per $mm^3$, or under 3,000 per $mm^3$. In some embodiments, the subject is a human patient having a total neutrophil granulocytes count under about 5,000 per $mm^3$, or under about 4,000 per $mm^3$, or under about 3,000 per $mm^3$, or under about 2,000 per $mm^3$, or under about 1,000 per $mm^3$. In some embodiments, the methods, compounds or compositions of the invention are effective in increasing the patients' total white blood cells count (and/or neutrophil granulocytes count) by at least 500 per $mm^3$, by at least 1,000 per $mm^3$, or by at least 2,000 per $mm^3$ or more.

Another aspect of the invention relates to the use of the compounds described herein for stimulating production of erythrocytes (i.e., erythropoiesis) in a subject and/or inhibiting decrease of erythrocytes (i.e., anemia) in a subject. Related aspects include using of these compounds for compensating for excessive blood loss (e.g., a hemorrhage or chronically through low-volume loss), excessive blood cell destruction (e.g., hemolysis) or deficient red blood cell production (e.g., ineffective hematopoiesis). Related aspects include using of these compounds for blood cell differentiation, including the stimulation of production of erythrocytes from erythroid progenitor cells.

Of particular interest to the inventors is addressing anemia associated with the use of chemotherapy or radiotherapy in the treatment of cancer. Also of particular interest is anemia associated with end-stage renal disease as is the case for patients who require regular dialysis or kidney transplantation for survival. Therefore, some aspects of the invention relates to methods, compounds and compositions for the stimulation of the hematopoietic system in humans, for instance for treating the myelosuppressive effects of chemotherapy and/or radiotherapy and any other situation in which the stimulation of the hematopoietic system can be of therapeutic value such as, but not limited to, anemia. Additional aspects of the invention relates to a method effective for increasing the efficacy of chemotherapy and/or radiation therapy in human patients. The methods, compounds and compositions according to the invention may also be useful for increasing the dose of chemotherapeutic compositions necessary to achieve a better therapeutic benefit, while avoiding increased side effects. Additional aspects relates to the methods, compounds and compositions according to the invention for reducing or eliminating chemotherapy-induced anemia in humans.

Typically, in normal adults, average values for red blood cell count (millions/mm$^3$), hemoglobin (g/100 mL) and hematocrit or volume packed red blood cells (mL/100 mL) for females and males (at sea level) are 4.8+/−0.6 and 5.4+/−0.9, 14.0+/−2.0 and 16.0+/−2.0 and 52.0+/−5.0 and 47.0+/−5.0 respectively. Anemia refers to the condition which exists when there is a reduction below normal in the number of erythrocytes, the quantity of hemoglobin or the volume of packed red blood cells in the blood as characterized by a determination of the hematocrit. In some embodiments, the subject is a human patient having an hematocrit between 40 and 30, or under about 40. In some embodiments, the methods, compounds or compositions of the invention are effective in slowing a decrease or maintaining the patients' total red blood cells count and/or hematocrit. In some embodiments, the methods, compounds or compositions of the invention are effective in stabilizing the patients' hematocrit and/or in increasing the hematocrit by up about 5, or about 10, or whatever is necessary to achieve a normal value. In some embodiments, the methods, compounds or compositions of the invention are effective in reducing the need for blood transfusion(s).

Inflammation

Another aspect of the invention relates to the use of the compounds of the invention for the prevention and/or treatment of inflammation-related diseases. The term "inflammation-related diseases" refers to any and all abnormalities associated with inflammation, including chronic and acute inflammatory diseases, including but not limited to immune mediated inflammatory disease (IMID) and autoimmune diseases arthritis, glomerulonephritis, vasculitis, psoriatic arthritis, systemic lupus erythematoses (SLE), idiopathic thrombocytopenic purpura (ITP), psoriasis, Still's disease (macrophage activation syndrome), uveitis, scleroderma, myositis, Reiter's syndrome, and Wegener's syndrome. Other examples of disorders associated with inflammation include, but not limited to, acne vulgaris, asthma, celiac disease, chronic prostatitis, hypersensitivities, pelvic inflammatory disease, inflammatory bowel diseases, reperfusion injury, sarcoidosis, transplant rejection, vasculitis, interstitial cystitis, Chroh'n disease, colitis, dermatitis, diverculitis, hepatitis, Parkinson's, atherosclerosis, Alzeimer and cancer. In addition, chronic inflammatory diseases like rheumatoid arthritis, inflammatory bowel disease, psoriasis, and liver disease cause "sickness behaviors," including fatigue, malaise, and loss of social interest. In general, prophylactic and therapeutic uses comprise administration of a compound as described herein to a subject, preferably a human patient in need thereof. The compounds of the invention may be administered with any conventional treatments, including more preferably the current treatments defined hereinbefore in the Background section. In order to evaluate, assess, and/or confirm the efficacy of the method, compounds and/or compositions of the invention, serial measurements can be undertaken. Quantitative methods and techniques for the measurement of inflammation are well known to the art and include, for example, methods similar to those provided in the exemplification section.

Kidney Protection

Still another aspect of the present invention relates to the use of compounds of the invention for preventing and/or treating a renal disorder in a subject in need thereof. The term "renal disorder", "renal disease" or "kidney disease" means any alteration in normal physiology and function of the kidney. This can result from a wide range of acute and chronic conditions and events, including physical, chemical or biological injury, insult, trauma or disease, such as for example nephrectomy, chemotherapy, hypertension, diabetes, congestive heart failure, lupus, sickle cell anemia and various inflammatory, infectious and autoimmune diseases, HIV-associated nephropathies etc. This term includes but is not limited to diseases and conditions such as kidney transplant, nephropathy; chronic kidney disease (CKD); glomerulonephritis; inherited diseases such as polycystic kidney disease; nephromegaly (extreme hypertrophy of one or both kidneys); nephrotic syndrome; end stage renal disease (ESRD); acute and chronic renal failure; interstitial disease; nephritis; sclerosis, an induration or hardening of tissues and/or vessels resulting from causes that include, for example, inflammation due to disease or injury; renal fibrosis and scarring; renal-associated proliferative disorders; and other primary or secondary pathological conditions. Fibrosis associated with dialysis following kidney failure and catheter placement, e.g., peritoneal and vascular access fibrosis, is also included. In some embodiments the present invention more particularly relates to methods, compounds and compositions for nephroprotection. As used herein, "nephroprotection" refers to a process by which the rate of disease progression in the kidney is delayed or stopped and so the kidney is subsequently protected. In preferred embodiments (e.g., drug-induced nephrotoxicity), the compounds of Formula I are administered prior to, during, or subsequent to the administration of a cytotoxic agent or anti-inflammatory or immunosuppressive drug. As used herein, "cytotoxic agent" refers to an agent which kills highly proliferating cells: e.g., tumors cells, virally infected cells, or hematopoietic cells. Examples of a cytotoxic agent include, but are not limited to, cyclophosphamide, doxorubicin, daunorubicin, vinblastine, vincristine, bleomycin, etoposide, topotecan, irinotecan, taxotere, taxol, 5-fluorouracil, methotrexate, gemcitabine, cisplatin, carboplatin, or chlorambucil, and an agonist of any of the above compounds. A cytotoxic agent can also be an antiviral agent: e.g., AZT (i.e., 3'-azido-3'-deoxythymidine) or 3TC/lamivudine (i.e., 3-thiacytidine). Such drugs can induce anemia in a mammal, including a human patient. In some embodiments, nephroprotection refers to the protection provided to a mammal from the toxic effects arising from treatment of the mammal with a chemotherapeutic agent. For instance, the compounds of Formula I or Formula II may be used to protect the mammal, or facilitate its recovery, from the toxic effects resulting from treatment with a chemotherapeutic agent.

In some embodiments, the renal disorder or kidney disease may be generally defined as a "nephropathy" or "nephropathies". The terms "nephropathy" or "nephropathies" encompass all clinical-pathological changes in the kidney which may result in kidney fibrosis and/or glomerular diseases (e.g., glomerulosclerosis, glomerulonephritis) and/or chronic renal insufficiency, and can cause end stage renal disease and/or renal failure. Some aspects of the present invention relate to compositions and their uses for the prevention and/or treatment of hypertensive nephropathy, diabetic nephropathy, and other types of nephropathy such as analgesic nephropathy, immune-mediated glomerulopathies (e.g., IgA nephropathy or Berger's disease, lupus nephritis), ischemic nephropathy, HIV-associated nephropathy, membranous nephropathy, glomerulonephritis, glomerulosclerosis, radiocontrast media-induced nephropathy, toxic nephropathy, analgesic-induced nephrotoxicity, cisplatin nephropathy, transplant nephropathy, and other forms of glomerular abnormality or injury; glomerular capillary injury (tubular fibrosis). In some embodiments, the terms "nephropathy" or "nephropathies" refers specifically to a disorder or disease where there is either the presence of proteins (i.e., proteinuria) in the urine of a subject and/or the presence of renal insufficiency.

The present invention further relates to methods, compounds and compositions for preventing and/or treating a renal disorder complication. The term "renal disorder complication" refers to a secondary condition correlated with a renal disorder, a health condition, an accident, or a negative reaction occurring during the course of a renal disorder that can become worse in its severity. A "renal disorder complication" is usually associated with increasing severity of the renal disease in the subjects suffering from symptoms or pathological changes, which can become widespread throughout the body or affecting other organ systems. As used herein, the term "renal disorder complication" encompasses, but is not limited to vascular diseases (e.g., macrovascular complications, microvascular complications, etc.), cardiovascular diseases (e.g., arteriosclerosis, atherosclerosis, coronary artery disease, congestive heart failure, stroke, angina, ischemic heat disease, myocardial infarction, etc.), diabetic dyslipidemia, hyperlipidemia (e.g., hypercholesterolemia, hypertriglyceridemia, hyperlipoproteinemia), metabolic syndrome, obesity, anemia, edema, pancreatitis, weak bones, poor nutritional health and nerve damage.

According to some embodiments, the present invention concerns methods, compounds and compositions for preventing or treating characteristic aspects or evidence nephropathy including glomerulosclerosis, modification of the kidney vascular structure, and tubulointerstitial disease. Among characteristic aspects of nephropathy contemplated by the invention is the prevention of kidney cell apoptosis, fibrosis, sclerosis, and/or accumulation of proteins in tubular regions. Therefore, in some aspects the invention relates to a method for the prevention of kidney cell apoptosis, fibrosis, sclerosis, and/or accumulation of proteins in tubular regions. Related aspects concerns the use of the compounds and pharmaceutical compositions as defined herein for reducing CTGF mRNA expression and/or TGF-β mRNA expression in kidney cells.

In some embodiments, the subject may be suffering from a disorder such as, for example, diabetes, advanced progressive renal disease, and fibrotic renal disease and/or any of the renal diseases, renal disorders or renal disorder complications described herein. In some embodiments, the subject is a human patient having or susceptible of having glomerular filtration problems and/or a renal failure. In some embodiments, the subject is a human patient who is following, or who has received, treatments of chemotherapy or radiotherapy. Accordingly, related aspect concerns using the compound or pharmaceutical composition as defined herein for protecting kidneys against chemotherapeutic agents, including, but not limited to, doxorubicin, daunorubicin, vinblastine, vincristine, bleomycin, taxol, 5-fluorouracil, methotrexate, gemcitabine, cisplastin, carboplatin and chlorambucil. The methods of the present invention may comprise administering to a subject, e.g., a human patient in need thereof, a preventative- or therapeutically-effective amount of a compound or pharmaceutical composition as defined herein.

In order to evaluate, assess, and/or confirm the efficacy of the method, compounds and/or compositions of the invention, serial measurements can be determined. Quantitative assessment of renal function and parameters of renal dysfunction are well known in the art and can be found, for example, in Levey (Am. J. Kidney Dis. 1993, 22(1):207-214). Examples of assays for the determination of renal function/dysfunction are: serum creatinine level; creatinine clearance rate; cystatin C clearance rate, 24-h urinary creatinine clearance, 24-h urinary protein secretion; Glomerular Filtration Rate (GFR); urinary albumin creatinine ratio (ACR); albumin excretion rate (AER); and renal biopsy. Accordingly, in some aspects, the invention relates to a method of increasing creatinine clearance, to method of increasing insulin secretion and/or increasing insulin sensitivity, to method of decreasing insulin resistance by administering to a subject in need thereof a compound of Formula I or Formula II.

In some embodiments, the subject is at risk of, or has been diagnosed with, nephropathy. Typically a normal Glomerular Filtration Rate (GFR) in humans is from about 100 to about 140 mL/min. In some embodiments, the subject is a human patient having advanced nephropathy (i.e., a GFR of under 75 mL/min). In some embodiments, the subject is a human patient having ESRD (i.e., GFR of less than 10 mL/min). In some embodiments, the methods, compounds or compositions of the invention are effective in increasing the patients' GFR value by at least 1, 5, 10, 15, 20 or 25 mL/min or more.

In some embodiments, the subject is at risk of, or has been diagnosed with, a kidney disease. In various embodiments, the subject is a human patient having or progressing towards stage I kidney disease, stage II kidney disease, stage III kidney disease, stage IV kidney disease or stage V kidney disease. In some embodiments, the methods, compounds or compositions of the invention are effective in stabilizing or in improving the patient's kidney disease (e.g., from stage V to stage IV, or from stage IV to stage III, or from stage III to stage II, or from stage II to stage I).

One of the first clinical indications of nephropathy is the presence of albuminuria or proteinuria. One refers to microalbuminuria when the amount of albumin in the urine is between 30 and 300 mg/day, macroalbuminuria or albuminuria when the amount of albumin in the urine is greater than 300 mg/day. One refers to proteinuria when the total amount of protein in the urine is greater than 0.5 g/day. In some embodiments, the subject is a human patient having microalbuminuria. In some embodiments, the subject is a human patient with an albumin amount in the urine that exceeds 300 mg/day. In some embodiments, the methods, compounds or compositions of the invention are effective in lowering the patient's albuminuria by at least 10, 25, 50, 75, 100, 150, 200 mg/day or more. According to some aspects, the invention related to a method of preventing or decreasing proteinuria by administering to a subject in need thereof a compound of Formula I or Formula II. In some embodiments, the subject is at risk of, or has been diagnosed with, proteinuria. In some embodiments, the subject is a human patient excreting between 0.5 to 4 g/day of protein in its urine. In some embodiments, the subject is a human patient excreting more than about 4 g/day of protein in its urine.

Effectiveness of the methods, compounds and compositions of the invention may be assessed by the reduction in the undesired symptoms. Such reduction may be determined for example by the improvement in renal function as compared to the function prior to treatment. Such remediation may be evident in a delay in the onset of renal failure (including dialysis or transplant) or in a decrease in the rate of the deterioration of renal function as determined for example by the slowing of the rate of the increase of proteinuria or slowing the rate of the rise in serum creatinine or by the fall in the parameter of creatinine clearance or GFR, or decrease in hospitalization rate or mortality. In preferred embodiments, the compound is Compound I, II, III, X or XXII, or a pharmaceutically acceptable salt thereof.

In one embodiment, a compound of the invention is used in combination with at least one additional known compound which is currently being used or in development for preventing or treating renal disorder such as nephropathy, or an associated disorder or complication. Examples of such known compounds include but are not limited to: ACE inhibitor drugs (e.g., captopril (Capoten®), enalapril (Innovace®), fosinopril (Staril®), lisinopril (Zestril®), perindopril (Coversyl®), quinapril (Accupro®), trandanalopril (Gopten®), lotensin, moexipril, ramipril); RAS blockers; angiotensin receptor blockers (ARBs) (e.g., Olmesartan, Irbesartan, Losartan, Valsartan, candesartan, eprosartan, telmisartan, etc.); protein kinase C (PKC) inhibitors (e.g., ruboxistaurin); inhibitors of AGE-dependent pathways (e.g., aminoguanidine, ALT-946, pyrodoxamine (pyrododorin), OPB-9295, alagebrium); anti-inflammatory agents (e.g., cyclooxigenase-2 inhibitors, mycophenolate mophetil, mizoribine, pentoxifylline), GAGs (e.g., sulodexide (U.S. Pat. No. 5,496,807)); pyridoxamine (U.S. Pat. No. 7,030,146); endothelin antagonists (e.g., SPP 301), COX-2 inhibitors, PPAR-γ antagonists and other compounds like amifostine (used for cisplatin nephropathy), captopril (used for diabetic nephropathy), cyclophosphamide (used for idiopathic membranous nephropathy), sodium thiosulfate (used for cisplatin nephropathy), tranilast, etc.

Fibrosis

Fibrosis refers to the formation or development of excess fibrous connective tissue in an organ that can occur as part of the wound healing process in damaged tissue. Fibrosis is to be differentiated from the normal process of wound healing whereby fibrous tissue forms as required by the organ and not in excess. Fibrosis, if not treated, gives rise to sclerosis which is an induration or hardening of tissue that leads to organ failure. At the cellular level, in response to normal tissue injury fibroblasts migrate into the wound where they synthesize and remodel new extracellular matrix. The fibroblast responsible for this process is referred to as the myofibroblast and it expresses the highly contractile protein α-smooth muscle actin. In normal tissue repair, the myofibroblast disappears. However, in fibrotic disease the myofibroblast remains at the injured tissue. The myofibroblast can arise by differentiation of the local resident fibroblast in response to growth factor proteins such as TFGβ and CTGF. The resident fibroblast has its genesis by means of tissue macrophages which differentiate via an intermediate cell type, the fibrocyte. Therefore, the fibrocyte has mixed characteristics of the stem cell, macrophage and fibroblast.

Still another aspect of the present invention relates to the use of compounds of Formula I and Formula II for preventing and/or treating a fibrosis-related disease or fibrosis-related organ dysfunction in a subject in need thereof. The term "fibrosis-related organ dysfunction" refers to any organ dysfunction or lesion(s) arising from fibrosis including, but not limited to dysfunction or lesion(s) of kidney, heart, lung, liver brain, bone marrow, soft tissue of the mediasteneum and retroperitoneum, skin, intestine and joints (knee, shoulder and others). The invention also encompasses fibrosis-related diseases involving an inflammatory and fibrotic response including, but not limited to endomyocardial fibrosis (heart), idiopathic pulmonary fibrosis (lung), cirrhosis (liver), myelofibrosis (bone marrow) and keloid and nephrogenic systemic fibrosis (skin). According to a particular embodiment, the compounds according to the invention have the ability to prevent and/or treat inflammation, as noted hereinbefore, and have the ability to prevent and/or treat any subsequent fibrosis.

In preferred embodiments, the organ is the kidney and the compounds described by Formula I and Formula II are for the prevention and/or treatment of kidney diseases. As noted hereinabove, renal tissue biopsy and subsequent lesion score may be useful for providing a definitive assessment of fibrotic disease and compound efficacy as a potential anti-fibrotic drug for kidney diseases. In addition, it might be possible to achieve a more indirect but convenient assessment of compound efficacy, thereby allowing the screening of the antifibrotic potential of a number of compounds, by measuring the ability of compounds of the present invention to induce the production of interleukin-12 (IL-12). IL-12 is a pro-inflammatory cytokine that is produced by macrophages (and dendritic cells) and it is known that IL-12 attenuates fibrosis. For example, M. Hesse, et al. in *Amer. J. Pathology* 157, 945-955 (2000) teaches that IL-12 exhibits an antifibrotic effect in a mouse model of granulomatous disease. Similarly, M. P. Keane et al. in *Amer. J. Physiol. Lung Cell Mol. Physiol.* 281, L92-L97 (2001) teaches that IL-12 attenuates bleomycin-induced pulmonary fibrosis in mice. In a mini-review by A. Bellini et al. in *Laboratory Investigation* 87, 858-870 (2007), it is reported that IL-12 inhibits the differentiation of fibrocytes.

E) Pharmaceutical Compositions and Formulations

A related aspect of the invention concerns pharmaceutical compositions comprising one or more of the compounds of the invention described herein (e.g., a compound of Formula I or Formula II). As indicated hereinbefore, the compounds of the invention may be useful in: (i) preventing and/or treating blood disorders (e.g., by stimulating hematopoiesis); (ii) preventing and/or treating a inflammation-related disease (e.g., an autoimmune disease); (iii) preventing, and/or treating a renal disorder and/or a renal disorder complication; and/or (iv) preventing and/or treating a fibrosis-related organ dysfunction.

As used herein, the term "therapeutically effective amount" means the amount of compound that, when administered to a subject for treating or preventing a particular disorder, disease or condition, is sufficient to effect such treatment or prevention of that disorder, disease or condition. Dosages and therapeutically effective amounts may vary for example, depending upon a variety of factors including the activity of the specific agent employed, the age, body weight, general health, gender, and diet of the subject, the time of administration, the route of administration, the rate of excretion, and any drug combination, if applicable, the effect which the practitioner desires the compound to have upon the subject and the properties of the compounds (e.g., bioavailability, stability, potency, toxicity, etc.), and the particular disorder(s) the subject is suffering from. In addition, the therapeutically effective amount may depend on the subject's blood parameters (e.g., lipid profile, insulin levels, glycemia), the severity of the disease state, organ function, or underlying disease or complications. Such appropriate doses may be determined using any available assays including the assays described herein. When one or more of the compounds of the invention is to be administered to humans, a physician may for example, prescribe a relatively low dose at first, subsequently increasing the dose until an appropriate response is obtained.

In general, however, the dose will be in the range from about 1 to about 100 mg/kg per day when administered orally; and in the range from about 0.01 to about 10 mg/kg per day when administered intravenously or subcutaneously. Preferably, the dose orally administered and is about 10 mg/kg. Preferably, the dose orally administered and is about 50 mg/kg.

As used herein, the term "pharmaceutical composition" refers to the presence of at least one compound of the invention according to Formula I or Formula II as defined herein and at least one pharmaceutically acceptable carrier, diluent, vehicle or excipient.

As used herein, the term "pharmaceutically acceptable carrier", "pharmaceutically acceptable diluent" or "pharmaceutically acceptable excipient" is intended to mean, without limitation, any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, emulsifier, or encapsulating agent, such as a liposome, cyclodextrins, encapsulating polymeric delivery systems or polyethyleneglycol matrix, which is acceptable for use in subjects, preferably humans. It preferably refers to a compound or composition that is approved or approvable by a regulatory agency of the Federal or State government or listed in the U.S. Pharmacopoeia or other generally recognized pharmacopoeia for use in animals and more particularly in humans. The pharmaceutically acceptable vehicle can be a solvent or dispersion medium containing, for example, water, ethanol, polyol (for example, glycerol, propylene glycol, and liquid polyethylene glycol), suitable mixtures thereof, and vegetable oils. Additional examples of pharmaceutically acceptable vehicles include, but are not limited to: Water for Injection USP; aqueous vehicles such as, but not limited to, Sodium Chloride Injection, Ringer's Injection, Dextrose Injection, Dextrose and Sodium Chloride Injection, and Lactated Ringer's Injection; water-miscible vehicles such as, but not limited to, ethyl alcohol, polyethylene glycol, and polypropylene glycol; and non-aqueous vehicles such as, but not limited to, corn oil, cottonseed oil, peanut oil, sesame oil, ethyl oleate, isopropyl myristate, and benzyl benzoate. Prevention of the action of microorganisms can be achieved by addition of antibacterial and antifungal agents, for example, parabens, chlorobutanol, phenol, ascorbic acid, thimerosal, and the like. In many cases, isotonic agents are included, for example, sugars, sodium chloride, or polyalcohols such as mannitol and sorbitol, in the composition. Prolonged absorption of injectable compositions can be brought about by including in the composition an agent which delays absorption, for example, aluminum monostearate or gelatin.

In some embodiments, the compositions of the invention comprise an effective amount of a compound of Formula I or Formula II. Preferred compounds are Compounds I, II, III, X or XXII.

In some embodiments, the invention pertains to pharmaceutical compositions for preventing and/or treating blood disorders that include one or more compounds of Formula I or Formula II.

In some embodiments, the invention pertains to pharmaceutical compositions for preventing and/or treating an inflammation-related disease that include one or more compounds of Formula I or Formula II.

In some embodiments, the invention pertains to pharmaceutical compositions for preventing and/or treating a renal disorder and/or a renal disorder complication that include one or more compounds of Formula I or Formula II.

In some embodiments, the invention pertains to pharmaceutical compositions for preventing and/or treating a fibrosis-related organ dysfunction that include one or more compounds of Formula I or Formula II.

The compounds of the invention may be formulated prior to administration into pharmaceutical compositions using available techniques and procedures. For instance, the pharmaceutical compositions may be formulated in a manner suitable for administration by oral, intravenous (iv), intramuscular (im), depo-im, subcutaneous (sc), depo-sc, sublingually, intranasal, intrathecal, topical or rectal routes.

Preferably, the compound(s) of the invention can be orally administered. The formulations may conveniently be presented in unit dosage form and may be prepared by any methods well known in the art of pharmacy. Methods of preparing these formulations or compositions include the step of bringing into association a compound of the present invention with a pharmaceutically acceptable vehicle (e.g., an inert diluent or an assimilable edible carrier) and, optionally, one or more accessory ingredients. In general, the formulations are prepared by uniformly and intimately bringing into association a compound of the present invention with liquid carriers, or finely divided solid carriers, or both, and then, if necessary, shaping the product. The amount of the therapeutic agent in such therapeutically useful compositions is such that a suitable dosage will be obtained.

Formulations of the invention suitable for oral administration may be in the form of capsules (e.g., hard or soft shell gelatin capsule), cachets, pills, tablets, lozenges, powders, granules, pellets, dragees, e.g., coated (e.g., enteric coated) or uncoated, or as a solution or a suspension in an aqueous or non-aqueous liquid, or as an oil-in-water or water-in-oil liquid emulsion, or as an elixir or syrup, or as pastilles or as mouth washes and the like, each containing a predetermined amount of a compound of the present invention as an active ingredient. A compound of the present invention may also be administered as a bolus, electuary or paste, or incorporated directly into the subject's diet. Moreover, in certain embodiments these pellets can be formulated to (a) provide for instant or rapid drug release (i.e., have no coating on them); (b) be coated, e.g., to provide for sustained drug release over time; or (c) be coated with an enteric coating for better gastrointestinal tolerability. Coating may be achieved by conventional methods, typically with pH or time-dependent coatings, such that the compound(s) of the invention is released in the vicinity of the desired location, or at various times to extend the desired action. Such dosage forms typically include, but are not limited to, one or more of cellulose acetate phthalate, polyvinylacetate phthalate, hydroxypropyl methyl cellulose phthalate, ethyl cellulose, waxes, and shellac.

In solid dosage forms for oral administration a compound of the present invention may be mixed with one or more pharmaceutically acceptable carriers, such as sodium citrate or dicalcium phosphate, or any of the following: fillers or extenders, such as starches, lactose, sucrose, glucose, mannitol, or silicic acid; binders, such as, for example, carboxymethylcellulose, alginates, gelatin, polyvinyl pyrrolidone, sucrose or acacia; humectants, such as glycerol; disintegrating agents, such as agar-agar, calcium carbonate, potato or tapioca starch, alginic acid, certain silicates, and sodium carbonate; solution retarding agents, such as paraffin; absorption accelerators, such as quaternary ammonium compounds; wetting agents, such as, for example, cetyl alcohol and glycerol monostearate; absorbents, such as kaolin and bentonite clay; lubricants, such as talc, calcium stearate, magnesium stearate, solid polyethylene glycols, sodium lauryl sulfate, and mixtures thereof; and coloring agents. In the case of capsules, tablets and pills, the pharmaceutical compositions may also comprise buffering agents. Solid compositions of a similar type may also be employed as fillers in soft and hard-filled gelatin capsules using such excipients as lactose or milk sugars, as well as high molecular weight polyethylene glycols and the like.

Peroral compositions typically include liquid solutions, emulsions, suspensions, and the like. The pharmaceutically acceptable vehicles suitable for preparation of such compositions are well known in the art. Typical components of carriers for syrups, elixirs, emulsions and suspensions include ethanol, glycerol, propylene glycol, polyethylene glycol, liquid sucrose, sorbitol and water. For a suspension, typical suspending agents include methyl cellulose, sodium carboxymethyl cellulose, tragacanth, and sodium alginate; typical wetting agents include lecithin and polysorbate 80; and typical preservatives include methyl paraben and sodium benzoate. Peroral liquid compositions may also contain one or more components such as sweeteners, flavoring agents and colorants disclosed above.

Pharmaceutical compositions suitable for injectable use may include sterile aqueous solutions (where water soluble) or dispersions and sterile powders for the extemporaneous preparation of sterile injectable solutions or dispersions. In all cases, the composition must be sterile and must be fluid to the extent that easy syringability exists. It must be stable under the conditions of manufacture and storage and must be preserved against the contaminating action of microorganisms such as bacteria and fungi. Sterile injectable solutions can be prepared by incorporating the therapeutic agent in the required amount in an appropriate solvent with one or a combination of ingredients enumerated above, as required, followed by filtered sterilization. Generally, dispersions are prepared by incorporating the therapeutic agent into a sterile vehicle which contains a basic dispersion medium and the required other ingredients from those enumerated above. In the case of sterile powders for the preparation of sterile injectable solutions, the methods of preparation are vacuum drying and freeze-drying which yields a powder of the active ingredient (i.e., the therapeutic agent) plus any additional desired ingredient from a previously sterile-filtered solution thereof.

Some pharmaceutical formulations may be suitable for administration as an aerosol, by inhalation. These formulations comprise a solution or suspension of the desired compound of Formula I or Formula II herein or a plurality of solid particles of such compound(s). For instance, metal salts of the compounds of this invention are expected to have physical chemical properties amenable with the preparation of fine particles of active pharmaceutical ingredient (API) for administration by inhalation but not the free acid form of these compounds. The desired formulation may be placed in a small chamber and nebulized. Nebulization may be accomplished by compressed air or by ultrasonic energy to form a plurality of liquid droplets or solid particles comprising the agents or salts. The liquid droplets or solid particles should have a particle size in the range of about 0.5 to about 5 microns. The solid particles can be obtained by processing the solid agent of any compound of Formula I or Formula II described herein, or a salt thereof, in any appropriate manner known in the art, such as by micronization. The size of the solid particles or droplets will be, for example, from about 1 to about 2 microns. In this respect, commercial nebulizers are available to achieve this purpose. A pharmaceutical formulation suitable for administration as an aerosol may be in the form of a liquid, the formulation will comprise a water-soluble agent of any Formula described herein, or a salt thereof, in a carrier which comprises water. A surfactant may be present which lowers the surface tension of the formulation sufficiently to result in the formation of droplets within the desired size range when subjected to nebulization.

The compositions of this invention may also be administered topically to a subject, e.g., by the direct laying on or spreading of the composition on the epidermal or epithelial tissue of the subject, or transdermally via a "patch". Such compositions include, for example, lotions, creams, solutions, gels and solids. These topical compositions may comprise an effective amount, usually at least about 0.1%, or even from about 1% to about 5%, of a compound of the invention. Suitable carriers for topical administration typically remain in place on the skin as a continuous film, and resist being removed by perspiration or immersion in water. Generally, the carrier is organic in nature and capable of having dispersed or dissolved therein the therapeutic agent. The carrier may include pharmaceutically acceptable emollients, emulsifiers, thickening agents, solvents and the like.

Other compositions useful for attaining systemic delivery of the subject agents may include sublingual, buccal and nasal dosage forms. Such compositions typically comprise one or more of soluble filler substances such as sucrose, sorbitol and mannitol; and binders such as acacia, microcrystalline cellulose, carboxymethyl cellulose and hydroxypropyl methyl cellulose. Glidants, lubricants, sweeteners, colorants, antioxidants and flavoring agents disclosed above may also be included.

The compound(s) of the invention may also be administered parenterally, intraperitoneally, intraspinally, or intracerebrally. For such compositions, the compound(s) of the invention can be prepared in glycerol, liquid polyethylene glycols, and mixtures thereof and in oils. Under ordinary conditions of storage and use, these preparations may contain a preservative to prevent the growth of microorganisms.

The method of treatment of the present invention may also include co-administration of the at least one compound according to the invention, or a pharmaceutically acceptable salt thereof together with the administration of another therapeutically effective agent for the prevention and/or treatment of (i) blood disorders, (ii) inflammation-related diseases, (iii) renal disorders and/or renal disorder complications, and (iv) fibrosis-related organ dysfunctions. Therefore, an additional aspect of the invention relates to methods of concomitant therapeutic treatment of a subject, comprising administering to a subject in need thereof an effective amount of a first agent and a second agent, wherein the first agent is as defined in Formula I or Formula II, and the second agent is for the prevention or treatment of any one of disorder or disease of (i) to (iv) hereinbefore. As used herein, the term "concomitant" or "concomitantly" as in the phrases "concomitant therapeutic treatment" or "concomitantly with" includes administering a first agent in the presence of a second agent. A concomitant therapeutic treatment method includes methods in which the first, second, third or additional agents are co-administered. A concomitant therapeutic treatment method also includes methods in which the first or additional agents are administered in the presence of a second or additional agents, wherein the second or additional agents, for example, may have been previously administered. A concomitant therapeutic treatment method may be executed step-wise by different actors. For example, one actor may administer to a subject a first agent and as a second actor may administer to the subject a second agent and the administering steps may be executed at the same time, or nearly the same time, or at distant times, so long as the first agent (and/or additional agents) are after administration in the presence of the second agent (and/or additional agents). The actor and the subject may be the same entity (e.g., a human).

Accordingly, the invention also relates to a method for preventing, reducing or eliminating a symptom or complication of any one of the above mentioned diseases or conditions. The method comprises administering, to a subject in need thereof, a first pharmaceutical composition comprising at least one compound of the invention and a second pharmaceutical composition comprising one or more additional active ingredients, wherein all active ingredients are administered in an amount sufficient to inhibit, reduce, or eliminate one or more symptoms or complications of the disease or condition to be treated. In one aspect, the administration of the first and second pharmaceutical composition is temporally spaced apart by at least about two minutes. Preferably the first agent is a compound of Formula I or Formula II as defined herein, or a pharmaceutically acceptable salt thereof, e.g., sodium salt. The second agent may be selected from the list of compounds given hereinbefore.

F) Kits

The compound(s) of the invention may be packaged as part of a kit, optionally including a container (e.g., packaging, a box, a vial, etc.). The kit may be commercially used according to the methods described herein and may include instructions for use in a method of the invention. Additional kit components may include acids, bases, buffering agents, inorganic salts, solvents, antioxidants, preservatives, or metal chelators. The additional kit components are present as pure compositions, or as aqueous or organic solutions that incorporate one or more additional kit components. Any or all of the kit components optionally further comprise buffers.

The compound(s) of the invention may or may not be administered to a patient at the same time or by the same route of administration. Therefore, the methods of the invention encompass kits which, when used by the medical practitioner, can simplify the administration of appropriate amounts of two or more active ingredients to a patient.

A typical kit of the invention comprises a unit dosage form of at least one compound according to the invention as defined by Formula I or Formula II as defined herein, or a pharmaceutically acceptable salt thereof, and a unit dosage form of at least one additional active ingredient. Examples of additional active ingredients that may be used in conjunction with the compounds of the invention include, but are not limited to, any of the compounds that could be used in combination with the compound(s) of the invention as indicated hereinbefore.

Kits of the invention can further comprise pharmaceutically acceptable vehicles that can be used to administer one or more active ingredients. For example, if an active ingredient is provided in a solid form that must be reconstituted for parenteral administration, the kit can comprise a sealed container of a suitable vehicle in which the active ingredient can be dissolved to form a particulate-free sterile solution that is suitable for parenteral administration. Examples of pharmaceutically acceptable vehicles are provided hereinbefore.

EXAMPLES

Instrumentation

All HPLC chromatograms and mass spectra were recorded on an HP 1100 LC-MS Agilent instrument using an analytical C18 column (250×4.6 mm, 5 microns) with a gradient over 5 min of 15-99% acetonitrile-water with 0.01% trifluoroacetic acid as the eluant and a flow of 2 mL/min.

Example 1

Synthesis of Compound I: Sodium (RS)-2-[4-Octanoylphenoxy]decanoate

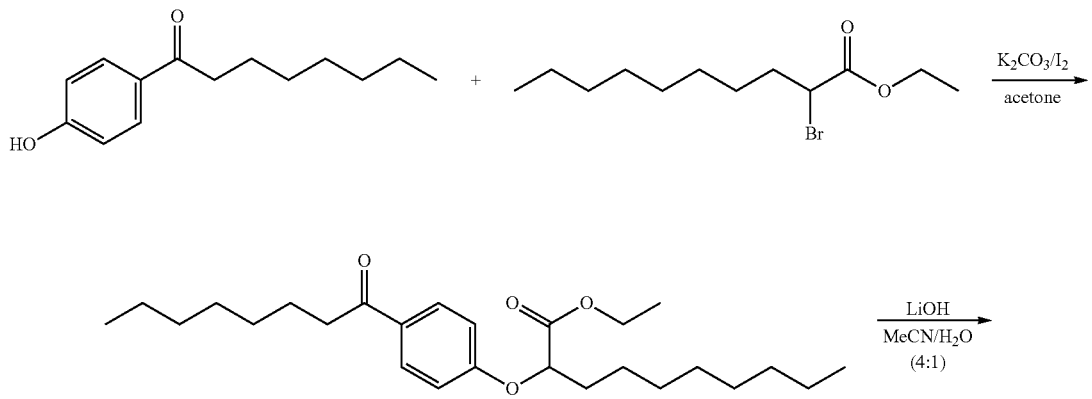

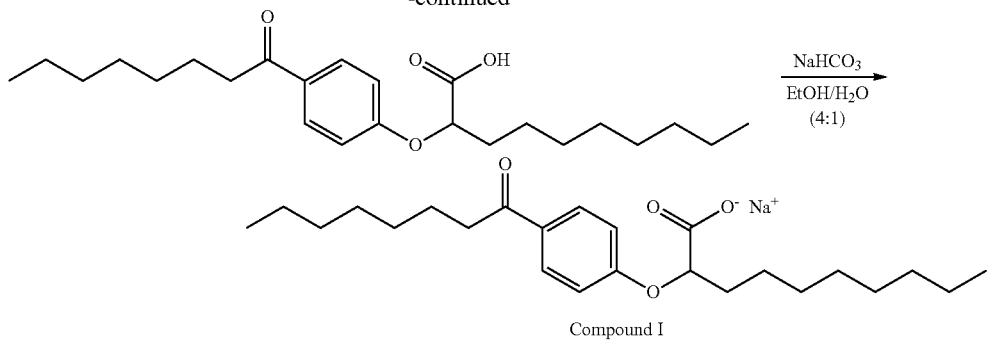

A mixture of 1-[4-hydroxyphenyl]octan-1-one (10.0 g, 45.4 mmol), K$_2$CO$_3$ (9.4 g, 68.1 mmol) and iodine (1.5 g, 9.1 mmol) in acetone (100 mL), was treated with ethyl 2-bromodecanoate (13.9 g, 49.9 mmol), and the reaction was stirred at room temperature, under nitrogen, overnight. Solvent was evaporated in vacuo, and the residue partitioned between ethyl acetate and water. The organic phase was washed with saturated sodium chloride, dried over magnesium sulfate, filtered and evaporated in vacuo. The crude material was purified on a silica gel pad, eluting with 5% ethyl acetate/hexane to give ethyl (RS)-2-[4-octanoylphenoxy]decanoate (11.9 g, 62%) as a colourless oil. $^1$H NMR (400 MHz, CDCl$_3$): δ 7.92 (d, J=9.0 Hz, 2H), 6.89 (d, J=9.0 Hz, 2H), 4.66 (dd, J=7.5, 5.2 Hz, 1H), 4.21 (q, J=7.0 Hz, 2H), 2.89 (t, J=7.4 Hz, 2H), 1.90-2.03 (m, 2H), 1.66-1.74 (m, 2H), 1.43-1.56 (m, 2H), 1.24-1.37 (m, 18H), 1.24 (t, J=7.2 Hz, 2H), 0.85-0.89 (m, 6H). A solution of ethyl ester (11.9 g, 28.3 mmol) in a mixture of tetrahydrofuran (360 mL), methanol (90 mL) and water (90 mL), was treated with lithium hydroxide monohydrate (5.9 g, 141.5 mmol), and the mixture was stirred at room temperature for 20 h. A second portion of lithium hydroxide monohydrate (2.3 g, 54.8 mmol) was added and the reaction was stirred at room temperature for an additional 3 h. The reaction mixture was concentrated in vacuo and the residue partitioned between ethyl acetate and water. The organic phase was washed with saturated sodium chloride, dried over magnesium sulfate, filtered and evaporated in vacuo, to give the crude product. Purification on a silica gel pad, eluting with 40% ethyl acetate/hexane; and recrystallization from hexanes gave (RS)-2-[4-octanoylphenoxy]decanoic acid (9.46 g, 86%) as a white solid. m.p. 45-47° C.; $^1$H NMR (400 MHz, CDCl$_3$): δ 7.93 (d, J=9.0 Hz, 2H), 6.91 (d, J=9.0 Hz, 2H), 4.72 (dd, J=6.8, 5.7 Hz, 1H), 2.90 (t, J=7.4 Hz, 2H), 1.98-2.04 (m, 2H), 1.67-1.74 (m, 2H), 1.46-1.59 (m, 2H), 1.24-1.37 (m, 18H), 0.87 (t, J=6.9 Hz, 3H), 0.88 (t, J=6.9 Hz, 3H). A solution of the acid (9.4 g, 24.1 mmol) in ethanol (200 mL) was treated with a solution of sodium bicarbonate (2.0 g, 24.1 mmol) in water (50 mL), and the reaction was stirred at room temperature for 5 h. Solvents were concentrated in vacuo, and the solution was diluted with water (950 mL), filtered (0.2 μm), and lyophilised to give sodium (RS)-2-[4-octanoylphenoxy]decanoate as a white solid (8.8 g, 88%). mp 275-280° C.; $^1$H NMR (400 MHz, CD$_3$OD): δ 7.96 (d, J=9.0 Hz, 2H), 6.97 (d, J=9.0 Hz, 2H), 4.72 (dd, J=6.2, 5.9 Hz, 1H), 2.95 (t, J=7.4 Hz, 2H), 1.94-1.99 (m, 2H), 1.64-1.72 (m, 2H), 1.49-1.57 (m, 2H), 1.28-1.40 (m, 18H), 0.90 (t, J=6.9 Hz, 3H), 0.89 (t, J=6.9 Hz, 3H); $^{13}$C NMR (101 MHz, CD$_3$OD): δ 200.72, 177.83, 163.37, 130.20, 129.61, 114.70, 79.55, 37.94, 33.19, 31.87, 31.76, 29.45, 29.38, 29.24, 29.22, 29.16, 25.74, 24.85, 22.57, 22.52, 13.29, 13.28; LRMS (ESI): m/z 391 (M−Na$^+$+2H$^+$); HPLC: 6 min. Resolution of the Enantiomers of Compound I.

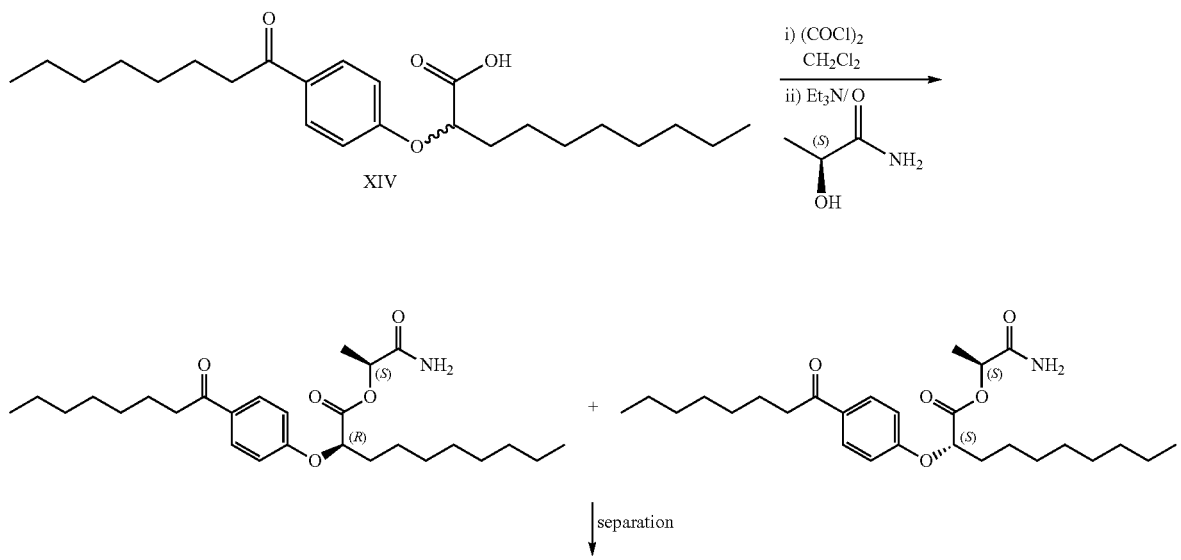

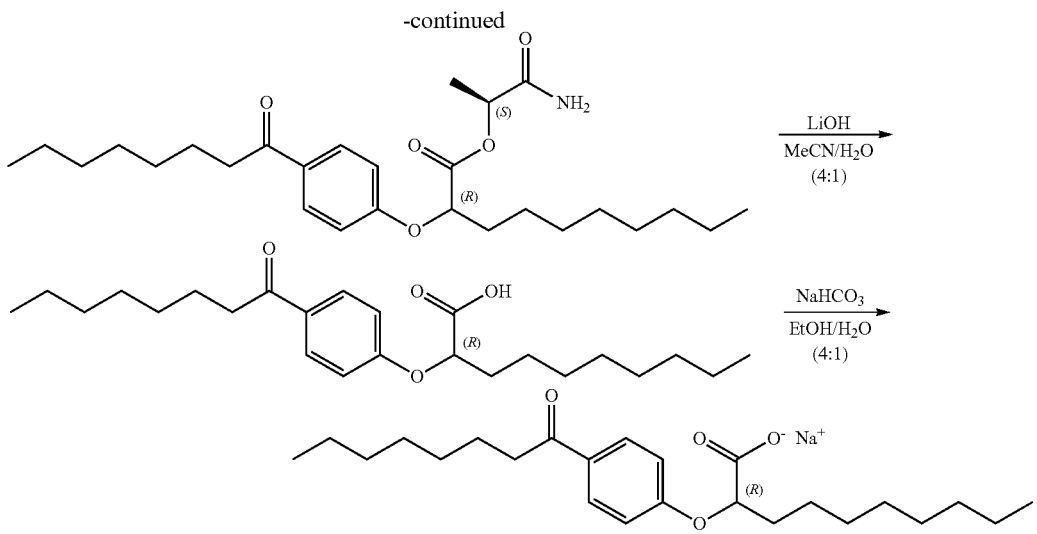

The same procedure was repeated for the (S) isomer

Sodium Salts of (R)- & (S)-2-[4-Octanoylphenoxy]decanoate

1) Formation and separation of (S)-lactamide esters: A solution of (RS)-2-[4-octanoylphenoxy]decanoic acid (0.9 g, 2.4 mL) in dichloromethane (20 mL) was treated dropwise with oxalyl chloride (0.26 mL, 3.1 mmol), and the reaction was stirred at room temperature for 1 h. Triethylamine (0.51 mL, 3.7 mmol) was added, followed by (S)-lactamide (0.5 g, 6.1 mmol), and the reaction was stirred at room temperature for 20 h. The solution was then diluted with ethyl acetate (100 mL), and washed with 1M aqueous HCl (100 mL), water (100 mL) and saturated sodium chloride (50 mL), then dried over sodium sulphate and evaporated in vacuo. The two diastereomers were separated on a Biotage™ 40 L column (silica), eluted with diethyl ether/hexane 1:4 to 1:1, then with ethyl acetate/hexane 1:4 to 1:1. This gave the separate pure diastereomers.

First diastereomer (0.51 g, 45%) as a white, waxy solid: $^1$H NMR (400 MHz, CDCl$_3$): δ 7.93 (d, J=9.0 Hz, 2H), 6.91 (d, J=8.8 Hz, 2H), 5.68 (br s, 1H), 5.54 (br s, 1H), 5.22 (q, J=6.8 Hz, 1H), 4.77 (dd, J=7.3, 5.2 Hz, 1H), 2.88 (t, J=7.5 Hz, 2H), 1.92-2.08 (m, 2H), 1.69, (tt, J=7.3, 7.3 Hz, 2H), 1.46-1.56 (m, 2H), 1.47, (d, J=6.8 Hz, 3H), 1.23-1.38 (m, 18H), 0.86 (t, J=6.6 Hz, 6H); $^{13}$C NMR (101 MHz, CDCl$_3$): δ 199.15, 172.34, 170.09, 161.35, 131.47, 130.82, 114.56, 76.70, 71.16, 38.59, 32.90, 32.00, 31.93, 29.57, 29.52, 29.35 (3C), 25.26, 24.68, 22.84 (2C), 17.85, 14.29 (2C).

Second diastereomer (0.5 g, 42%) as a viscous, colourless oil: $^1$H NMR (400 MHz, CDCl$_3$): δ 7.90 (d, J=9.0 Hz, 2H), 6.91 (d, J=9.0 Hz, 2H), 6.25 (br s, 1H), 6.15 (br s, 1H), 5.20 (q, J=6.9 Hz, 1H), 4.79 (dd, J=6.6, 5.9 Hz, 1H), 2.88 (t, J=7.5 Hz, 2H), 1.95-2.01 (m, 2H), 1.68, (tt, J=7.3, 7.3 Hz, 2H), 1.47-1.55 (m, 2H), 1.39, (d, J=6.8 Hz, 3H), 1.22-1.37 (m, 18H), 0.86 (t, J=6.8 Hz, 6H); $^{13}$C NMR (101 MHz, CDCl$_3$): δ 199.43, 172.71, 170.29, 161.52, 131.31, 130.60, 114.84, 76.48, 71.13, 38.59, 32.80, 32.00, 31.93, 29.58, 29.53, 29.36 (3C), 25.36, 24.76, 22.84 (2C), 17.69, 14.29 (2C).

2) Conversion of Diastereomers to the Corresponding Sodium Salt:

General Procedure:

A solution of diastereomeric ester (1.7 g, 3.7 mmol) in acetonitrile (72 mL) was treated with a solution of lithium hydroxide (0.5 g, 18.7 mmol) in water (18 mL), and the reaction was stirred at room temperature for 17 h. The reaction was quenched by addition of 1M aqueous HCl (150 mL), and extracted with ethyl acetate (2×100 mL). Combined extracts were washed with water (150 mL) and saturated sodium chloride (150 mL); then dried over sodium sulfate, filtered and evaporated in vacuo to give the crude acid.

First Enantiomer (Higher R$_f$, Silica Gel):

Purification on a Biotage™ 40 L column (silica), eluted with ethyl acetate/hexane 1:9 to 7:3, gave the purified acid enantiomer as a white solid (1.3 g, 87%). $^1$H NMR (400 MHz, CDCl$_3$): δ 11.50 (s, 1H), 7.92 (d, J=8.8 Hz, 2H), 6.90 (d, J=9.0 Hz, 2H), 4.71 (dd, J=6.4, 5.9 Hz, 1H), 2.89 (t, J=7.4 Hz, 2H), 1.97-2.03 (m, 2H), 1.69, (tt, J=7.1, 7.1 Hz, 2H), 1.45-1.59 (m, 2H), 1.21-1.38 (m, 18H), 0.862 (t, J=7.0 Hz, 3H), 0.859 (t, J=6.8 Hz, 3H); $^{13}$C NMR (101 MHz, CDCl$_3$): δ 200.20, 176.59, 161.76, 131.00, 130.77, 114.83, 76.15, 38.59, 32.80, 32.03, 31.93, 29.59, 29.53, 29.39, 29.37 (2C), 25.38, 24.91, 22.89 (2C), 14.30 (2C). A solution of the acid (1.3 g, 3.2 mmol) in ethanol (20 mL) was treated with a solution of sodium bicarbonate (0.3 g, 3.2 mmol) in water (5 mL), and the reaction was stirred at room temperature for 3 days. Solvents were evaporated in vacuo to give the crude salt as a white waxy solid. This material was dissolved in water (130 mL), filtered (0.2 micron; nylon) and lyophilised to give the pure enantiomer as a white solid (1.1 g, 97%). $^1$H NMR (400 MHz, CD$_3$OD): δ 7.91 (d, J=8.6 Hz, 2H), 6.96 (d, J=8.8 Hz, 2H), 4.46 (t, J=6.2 Hz, 1H), 2.92 (t, J=7.3 Hz, 2H), 1.90-1.95 (m, 2H), 1.66, (tt, J=7.2, 7.2 Hz, 2H), 1.44-1.61 (m, 2H), 1.24-1.39 (m, 18H), 0.890 (t, J=6.7 Hz, 3H), 0.882 (t, J=6.7 Hz, 3H); $^{13}$C NMR (101 MHz, CD$_3$OD): δ 200.66, 177.83, 163.37, 130.24, 129.64, 114.73, 79.59, 37.96, 33.20, 31.87, 31.76, 29.46, 29.40, 29.26, 29.22, 29.16, 25.75, 24.86, 22.57, 22.53, 13.32, 13.29; other data to be collected.

Second Enantiomer (Lower R$_f$, Silica Gel):

Purification on a Biotage™ 40L column (silica), eluted with ethyl acetate/hexane 1:9 to 7:3, gave the purified acid enantiomer as a white solid (1.1 g, 87%). $^1$H NMR (400 MHz, CDCl$_3$): δ 11.51 (s, 1H), 7.91 (d, J=9.0 Hz, 2H), 6.90 (d, J=9.0 Hz, 2H), 4.71 (dd, J=6.6, 5.9 Hz, 1H), 2.89 (t, J=7.5 Hz, 2H), 1.97-2.03 (m, 2H), 1.69, (tt, J=7.1, 7.1 Hz, 2H), 1.45-1.58 (m, 2H), 1.21-1.37 (m, 18H), 0.862 (t, J=7.0 Hz, 3H), 0.858 (t, J=7.0 Hz, 3H); $^{13}$C NMR (101 MHz, CDCl$_3$): δ 200.16, 176.47, 161.77, 131.03, 130.76, 114.84, 76.18, 38.58, 32.79, 32.02, 31.93, 29.58, 29.52, 29.37, 29.36 (2C), 25.36, 24.91, 22.84 (2C), 14.35, 14.28. A solution of the acid (1.1 g, 2.7 mmol) in ethanol (16 mL) was treated with a solution of sodium bicarbonate (0.2 g, 2.7 mmol) in water (4 mL), and the reaction was stirred at room temperature for 18 h. Solvent was evaporated in vacuo to give the crude salt as a clear, colourless syrup. This material was dissolved in water (100 mL), filtered (0.2 micron; nylon) and lyophilised to give the pure enantiomer as a white solid (1.1 g, 99%). $^{1}$H NMR (400 MHz, CD$_3$OD): δ 7.91 (d, J=9.0 Hz, 2H), 6.96 (d, J=9.0 Hz, 2H), 4.46 (t, J=6.2 Hz, 1H), 2.92 (t, J=7.4 Hz, 2H), 1.90-1.95 (m, 2H), 1.66, (tt, J=7.1, 7.1 Hz, 2H), 1.45-1.61 (m, 2H), 1.24-1.39 (m, 18H), 0.890 (t, J=6.8 Hz, 3H), 0.881 (t, J=6.9 Hz, 3H); $^{13}$C NMR (101 MHz, CD$_3$OD): δ 200.65, 177.82, 163.37, 130.20, 129.65, 114.74, 79.58, 37.96, 33.19, 31.87, 31.76, 29.46, 29.40, 29.26, 29.22, 29.16, 25.75, 24.86, 22.57, 22.53, 13.32, 13.29.

Example 2

Sodium 3-Octanoylbenzoate

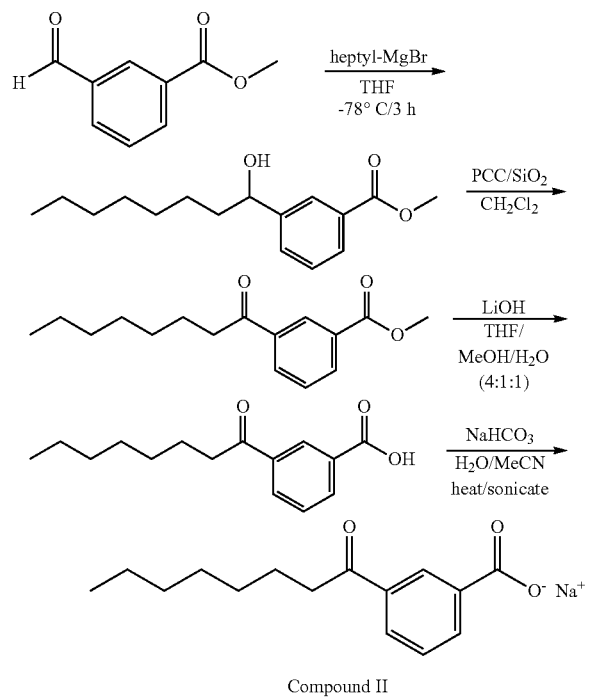

Compound II

A solution of methyl 3-formylbenzoate (2.0 g, 12.2 mmol) in tetrahydrofuran (40 mL) was cooled to −78° C. under nitrogen. A solution of n-heptylmagnesium bromide in tetrahydrofuran (1M; 12.2 mL, 12.2 mmol) was added dropwise over 30 min, and the reaction was stirred at −78° C. for 3 h. The reaction was quenched by addition of aqueous HCl (1M), and the mixture was extracted (3×) with ethyl acetate. Extracts were combined, dried over sodium sulfate, filtered and evaporated in vacuo. The crude material was purified on a Biotage™ 40 M column (silica), eluting with 10% ethyl acetate/hexane to give methyl (RS)-3-[1-hydroxyoctyl]benzoate (2.2 g, 69%) as a colourless oil. $^{1}$H NMR (400 MHz, CDCl$_3$): δ 7.98 (s, 1H), 7.91 (d, J=7.8 Hz, 1H), 7.53 (d, J=7.8 Hz, 1H), 7.39 (dd, J=7.8, 7.8 Hz, 1H), 4.65-4.71 (s, 1H), 3.89 (s, 3H), 2.33 (d, J=3.1 Hz, 1H), 1.62-1.80 (m, 2H), 1.18-1.41 (m, 10H), 0.85 (t, J=6.9 Hz, 3H). A solution of the secondary alcohol (2.0 g, 7.5 mmol) in dichloromethane (50 mL) was treated with silica gel (16 g) and pyridinium chlorochromate (3.2 g, 15.0 mmol), and the reaction was stirred at room temperature overnight. The reaction mixture was filtered through silica gel, and the residue was washed with dichloromethane. Combined filtrate and washings were evaporated in vacuo to give methyl 3-octanoylbenzoate (9.5 g, 86%). $^{1}$H NMR (400 MHz, CDCl$_3$): δ 8.58-8.59 (m, 1H), 8.20-8.23 (m, 1H), 8.14-8.17 (m, 1H), 7.53-7.57 (m, 1H), 3.95 (s, 3H), 3.00 (t, J=7.3 Hz, 2H), 1.74 (tt, J=7.3, 7.3 Hz, 2H), 1.24-1.40 (m, 8H), 0.88 (t, J=6.9 Hz, 3H). A solution of the methyl ester (1.0 g, 3.8 mmol) in tetrahydrofuran (30 mL), was treated with a solution of lithium hydroxide monohydrate (800 mg, 19.1 mmol) in water (7 mL). Methanol (7 mL) was then added, and the mixture was stirred at room temperature for 24 h. The reaction mixture was treated with aqueous HCl (1 M) until the pH was below 5, and was then extracted with ethyl acetate (3×). Organic extracts were combined, washed with saturated aqueous sodium chloride, dried over sodium sulfate, filtered and evaporated in vacuo, to give 3-octanoylbenzoic acid (919 mg, 97%). $^{1}$H NMR (400 MHz, CD$_3$OD): δ 8.59 (dd, J=1.7, 1.2 Hz, 1H), 8.18-8.24 (m, 2H), 7.61 (ddd, J=7.8, 7.8, 0.4 Hz, 1H), 3.05 (t, J=7.3 Hz, 2H), 1.71 (tt, J=7.3, 7.3 Hz, 2H), 1.27-1.41 (m, 8H), 0.90 (t, J=7.0 Hz, 3H). A mixture of the acid (919 mg, 3.7 mmol) and sodium bicarbonate (311 mg, 3.7 mmol) was treated with water (20 mL), and the reaction heated with sonication and stirred until most of the solids dissolved. Acetonitrile was added and the mixture was filtered (0.45 µm), and lyophilised to give sodium 3-octanoylbenzoate as a white solid (1.0 g, 100%). $^{1}$H NMR (400 MHz, D$_2$O): δ 8.14 (s, 1H), 7.81 (d, J=7.8 Hz, 1H), 7.61 (d, J=8.0 Hz, 1H), 7.18 (dd, J=8.0, 7.8 Hz, 1H), 2.69 (t, J=6.8 Hz, 2H), 1.33 (tt, J=7.0, 7.0 Hz, 2H), 0.88-1.03 (m, 8H), 0.54 (t, J=7.0 Hz, 3H). $^{13}$C NMR (101 MHz, D$_2$O): δ 203.93, 173.62, 137.25, 136.27, 133.92, 130.27, 128.59, 128.48, 38.58, 31.41, 28.82, 28.79, 24.25, 22.32, 13.60; LRMS (ESI): m/z 249 (M−Na$^+$+2H$^+$); HPLC: 4 min.

Example 3

Sodium (RS)-5-Octanoylindane-2-carboxylate

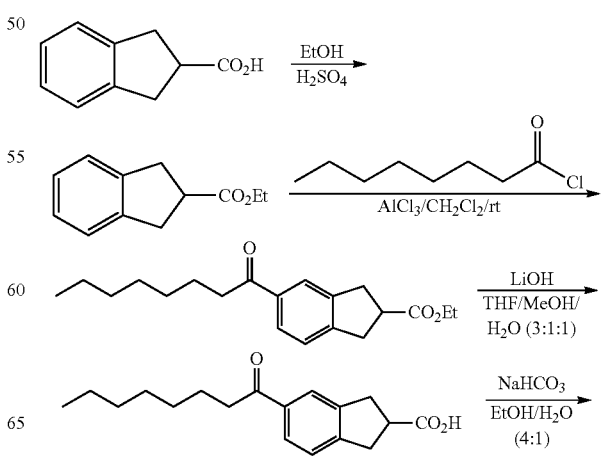

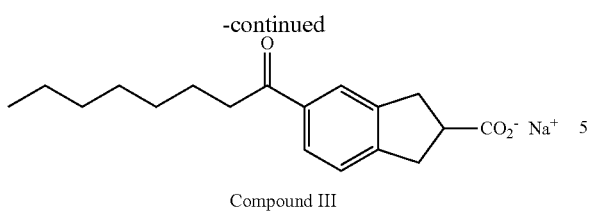

Compound III

A solution of indane-2-carboxylic acid (504 mg, 3.1 mmol) and sulphuric acid (2 mL) in dry ethanol, was heated at 75° C. for 3 days. The solution was concentrated in vacuo, and then partitioned between dichloromethane and water. The pH of the aqueous layer was adjusted to 13-14 with aqueous sodium hydroxide (5 M), and the layers were separated. The aqueous phase was diluted with saturated sodium chloride, and extracted (2×) with dichloromethane. Combined organic extracts were washed with saturated sodium chloride, dried over sodium sulfate, filtered and evaporated in vacuo, to give the crude product. Purification on a Biotage™ 25S column (silica), eluting with 3% ethyl acetate/hexane, gave ethyl indane-2-carboxylate (526 mg, 96%). $^1$H NMR (400 MHz, CDCl$_3$): δ 7.22-7.26 (m, 2H), 7.17-7.20 (m, 2H), 4.21 (q, J=7.0 Hz, 2H), 3.19-3.39 (m, 5H), 1.31 (t, J=7.0 Hz, 3H). A mixture of ethyl indane-2-carboxylate (100 mg, 0.5 mmol) and aluminium chloride (164 mg, 1.2 mmol) in dichloromethane (4 mL), was treated with octanoyl chloride (0.1 mL, 0.5 mmol) at room temperature, and the reaction was stirred at ambient temperature overnight. The reaction mixture was poured onto a mixture of ice and aqueous. Hydrochloric acid (1 M), and extracted (3×) with dichloromethane. Combined organic extracts were dried over magnesium sulfate, filtered and evaporated in vacuo. The crude material was purified on a Biotage™ column (silica), eluting with 5% ethyl acetate/hexane, to give ethyl (RS)-5-octanoyl-indane-2-carboxylate (110 mg, 65%). $^1$H NMR (400 MHz, CDCl$_3$): δ 7.69-7.77 (m, 2H), 7.29-7.32 (m, 1H), 4.07-4.17 (m, 2H), 3.15-3.36 (m, 5H), 2.84-2.90 (m, 2H), 1.62-1.70 (m, 2H), 1.19-1.34 (m, 8H), 0.80-0.87 (m, 3H) A suspension of the ethyl ester (82 mg, 0.3 mmol) in a mixture of tetrahydrofuran (3 mL), methanol (1 mL) and water (1 mL), was treated with lithium hydroxide (43 mg, 1.8 mmol), and the mixture was stirred at room temperature overnight. The reaction mixture was concentrated in vacuo and the residue diluted with water. The pH was adjusted to pH 4 with aqueous HCl (1M), and the mixture was extracted (3×) with ethyl acetate. Combined organic extracts were dried over magnesium sulfate, filtered and evaporated in vacuo, to give the crude product. Purification on a Biotage™ 12 M column (silica), eluting with 2% ethyl acetate/hexane, gave (RS)-5-octanoyl-indane-2-carboxylic acid (60 mg, 80%). $^1$H NMR (400 MHz, CD$_3$OD): δ 7.80 (s, 1H), 7.78 (dd, J=7.8, 1.4 Hz, 1H), 7.30 (d, J=7.8 Hz, 1H), 3.36 (tt, J=8.2, 8.2 Hz, 1H), 3.24 (d, J=8.2 Hz, 4H), 2.96 (t, J=7.4 Hz, 2H), 1.67 (tt, J=7.2, 7.2 Hz, 2H), 1.26-1.39 (m, 8H), 0.89 (t, J=6.9 Hz, 3H). A solution of the acid (60 mg, 0.2 mmol) in ethanol (4 mL) and water (1 mL) was treated with sodium bicarbonate (18 mg, 0.2 mmol), and the reaction was stirred at room temperature overnight. Solvents were concentrated in vacuo, and the solution was diluted with water, filtered (20 μm), and lyophilized to give sodium (RS)-5-octanoyl-indane-2-carboxylate as a white solid (54 mg, 87%). $^1$H NMR (400 MHz, CD$_3$OD): δ 7.91 (s, 1H), 7.76 (dd, J=7.8, 1.6 Hz, 1H), 7.28 (d, J=7.8 Hz, 1H), 3.16-3.25 (m, 5H), 2.97 (t, J=7.3 Hz, 2H), 1.68 (tt, J=7.3, 7.3 Hz, 2H), 1.28-1.40 (m, 8H), 0.90 (t, J=7.0 Hz, 3H); LRMS (ESI): m/z 289 (M−Na$^+$+2H$^+$); HPLC: 5 min.

Example 4

Synthesis of Compound VIII: Sodium (RS)-2-[4-Octanoylphenoxy]octanoate

1-[4-Hydroxyphenyl]-1-octanone (440 mg, 2.0 mmol) and ethyl (RS)-2-bromooctanoate (552 mg, 2.2 mmol) were reacted according to the procedure used for the preparation of Compound I to give Ethyl (RS)-2-[4-Octanoylphenoxy]octanoate (605 mg, 78%). $^1$H NMR (400 MHz, CDCl$_3$): δ 7.91 (d, J=9.0 Hz, 2H), 6.88 (d, J=9.0 Hz, 2H), 4.66 (dd, J=5.1, 7.4 Hz, 1H), 4.20 (q, J=7.0 Hz, 2H), 2.88 (t, J=7.5 Hz, 2H), 1.88-2.02 (m, 2H), 1.70 (tt, J=7.2, 7.2 Hz, 2H), 1.41-1.56 (m, 2H), 1.25-1.37 (m, 14H), 1.23 (t, J=7.1 Hz, 3H), 0.87 (t, J=7.2 Hz, 3H), 0.86 (t, J=7.2 Hz, 3H); $^{13}$C NMR (101 MHz, CDCl$_3$): δ 199.41, 171.48, 161.81, 131.01, 130.54 (2C), 114.77 (2C), 76.75, 61.62, 38.56, 32.90, 31.94, 31.78, 29.60, 29.38, 29.07, 25.33, 24.80, 22.85, 22.75, 14.39, 14.31, 14.26. The resulting ester (605 mg, 1.6 mmol) was saponified with lithium hydroxide (186 mg, 7.8 mmol) according to the procedure used for the preparation of Compound I to give (RS)-2-[4-Octanoylphenoxy]octanoic Acid (487 mg, 87%). $^1$H NMR (400 MHz, CDCl$_3$): δ 9.70 (br s, 1H), 7.89 (d, J=9.0 Hz, 2H), 6.89 (d, J=9.0 Hz, 2H), 4.69 (dd, J=5.9, 6.6 Hz, 1H), 2.87 (t, J=7.5 Hz, 2H), 1.95-2.01 (m, 2H), 1.67 (tt, J=7.2, 7.2 Hz, 2H), 1.43-1.58 (m, 2H), 1.24-1.37 (m, 14H), 0.851 (t, J=6.8 Hz, 3H), 0.849 (t, J=7.4 Hz, 3H); $^{13}$C NMR (101 MHz, CDCl$_3$): δ 200.38, 176.08, 161.84, 130.85, 130.78 (2C), 114.83 (2C), 76.20, 38.56, 32.79, 31.93, 31.76, 29.57, 29.35, 29.05, 25.34, 24.92, 22.84, 22.74, 14.29, 14.23. The acid (500 mg, 1.4 mmol) was then converted to the sodium salt according to the procedure used for the preparation of Compound I to give Sodium (RS)-2-[4-Octanoylphenoxy]octanoate (404 mg, 76%) as a white solid. mp 165-170° C.; $^1$H NMR (400 MHz, CD$_3$OD): δ 7.91 (d, J=8.8 Hz, 2H), 6.95 (d, J=8.8 Hz, 2H), 4.58 (dd, J=6.1, 6.3 Hz, 1H), 2.91 (t, J=7.3 Hz, 2H), 1.91-1.96 (m, 2H), 1.62-1.69 (m, 2H), 1.44-1.58 (m, 2H), 1.25-1.39 (m, 14H), 0.87-0.90 (m, 6H); $^{13}$C NMR (101 MHz, CD$_3$OD): δ 200.50, 176.40, 162.96, 130.28 (2C), 129.94, 114.71 (2C), 78.38, 38.00, 32.98, 31.79, 31.74, 29.27, 29.20, 29.05, 25.50, 24.79, 22.56, 22.51, 13.36, 13.34; LRMS (ESI): m/z 769 (M$_2$H$^+$), 748 (2M−Na$^+$+2H$^+$), 363 (M−Na$^+$+2H$^+$); HPLC: 3 min.

Example 5

Synthesis of Compound IX: Sodium (RS)-2-[4-Butyrylphenoxy]decanoate

1-[4-Hydroxyphenyl]-1-butanone (328 mg, 2.0 mmol) and ethyl (RS)-2-bromodecanoate (614 mg, 2.2 mmol) were reacted according to the procedure used for the preparation of Compound I to give Ethyl (RS)-2-[4-Butyrylphenoxy]decanoate (616 mg, 85%) as a clear, colourless oil. $^1$H NMR (400 MHz, CDCl$_3$): δ 7.88 (d, J=9.0 Hz, 2H), 6.86 (d, J=9.0 Hz, 2H), 4.64 (dd, J=5.7, 6.8 Hz, 1H), 4.17 (q, J=7.2 Hz, 2H), 2.83 (t, J=7.3 Hz, 2H), 1.85-1.99 (m, 2H), 1.65-1.75 (m, 2H), 1.39-1.44 (m, 2H), 1.22-1.34 (m, 10H), 1.20 (t, J=7.2 Hz, 3H), 0.94 (t, J=7.4 Hz, 3H), 0.83 (t, J=7.0 Hz, 3H); $^{13}$C NMR (101 MHz, CDCl$_3$): δ 199.04, 171.39, 161.80, 130.98, 130.48 (2C), 114.74 (2C), 76.68, 61.55, 40.37, 32.85, 32.01, 29.53, 29.37 (2C), 25.33, 22.84, 18.11, 14.34, 14.29, 14.10. The resulting ester (616 mg, 1.70 mmol) was saponified with lithium hydroxide (203 mg, 8.5 mmol) according to the procedure used for the preparation of Compound I to give (RS)-2-[4-Butyrylphenoxy]decanoic Acid (166 mg, 29%). $^1$H NMR (400 MHz, CDCl$_3$): δ 10.06 (br s, 1H), 7.91 (d, J=9.0 Hz, 2H), 6.90 (d, J=9.0 Hz, 2H), 4.70 (dd, J=5.9, 6.4 Hz, 1H), 2.87 (t, J=7.3 Hz, 2H), 1.96-2.02 (m, 2H), 1.68-1.77 (m, 2H), 1.44-1.59 (m, 2H), 1.24-1.37 (m, 10H), 0.97 (t, J=7.4 Hz, 3H), 0.86 (t, J=7.0 Hz, 3H); $^{13}$C NMR (101 MHz, CDCl$_3$): δ 199.95, 176.56, 161.74, 131.03, 130.73 (2C), 114.82 (2C), 76.16, 40.47, 32.79, 32.03, 29.53, 29.39, 29.37, 25.38, 22.86, 18.26, 14.31, 14.12. The acid (166 mg, 0.5 mmol) was then converted to the sodium salt according to the procedure used for the preparation of Compound I to give Sodium (RS)-2-[4-Butyrylphenoxy]decanoate (149 mg, 85%) as a white solid. mp 262-278° C.; $^1$H NMR (400 MHz, CD$_3$OD): δ 7.91 (d, J=9.0 Hz, 2H), 6.96 (d, J=9.0 Hz, 2H), 4.70 (dd, J=6.1, 6.5 Hz, 1H), 2.90 (t, J=7.3 Hz, 2H), 1.88-1.93 (m, 2H), 1.67 (tq, J=7.4, 7.4 Hz, 2H), 1.41-1.57 (m, 2H), 1.20-1.35 (m, 10H), 0.95 (t, J=7.4 Hz, 3H), 0.83 (t, J=6.9 Hz, 3H); $^{13}$C NMR (101 MHz, CD$_3$OD): δ 201.82, 178.07, 163.36, 130.53 (2C), 129.54, 114.83 (2C), 79.46, 39.99, 33.11, 31.80, 29.40, 29.27, 29.15, 25.72, 22.54, 18.30, 14.46, 14.15; LRMS (ESI): m/z 713 (M$_2$H$^+$), 669 (2M−2Na$^+$+3H$^+$), 335 (M−Na$^+$+2H$^+$); HPLC: 3 min.

Example 6

Synthesis of Compound X: Sodium (RS)-2-[4-Hexanoylphenoxy]decanoate

1-[4-Hydroxyphenyl]-1-hexanone (384 mg, 2.0 mmol) and ethyl (RS)-2-bromodecanoate (614 mg, 2.2 mmol) were reacted according to the procedure used for the preparation of Compound I to give Ethyl (RS)-2-[4-Hexanoylphenoxy]decanoate (628 mg, 80%). $^1$H NMR (400 MHz, CDCl$_3$): δ 7.86 (d, J=9.0 Hz, 2H), 6.84 (d, J=9.0 Hz, 2H), 4.60-4.65 (m, 1H), 4.15 (q, J=7.0 Hz, 2H), 2.83 (t, J=7.3 Hz, 2H), 1.86-1.97 (m, 2H), 1.61-1.70 (m, 2H), 1.38-1.52 (m, 2H), 1.20-1.34 (m, 14H), 1.18 (t, J=7.2 Hz, 3H), 0.78-0.87 (m, 6H); $^{13}$C NMR (101 MHz, CDCl$_3$): δ 199.17, 171.36, 161.78, 130.95, 130.46 (2C), 114.72 (2C), 76.66, 61.51, 38.41, 32.84, 32.00, 31.76, 29.52, 29.35 (2C), 25.31, 24.41, 22.83, 22.74, 14.33, 14.26, 14.14. The resulting ester (628 mg, 1.6 mmol) was saponified with lithium hydroxide (193 mg, 8.0 mmol) according to the procedure used for the preparation of Compound I to give (RS)-2-[4-Hexanoylphenoxy]decanoic Acid (468 mg, 80%). $^1$H NMR (400 MHz, CDCl$_3$): δ 7.93 (d, J=9.0 Hz, 2H), 6.91 (d, J=9.0 Hz, 2H), 5.77 (br s, 1H), 4.70 (dd, J=5.8, 6.6 Hz, 1H), 2.89 (t, J=7.4 Hz, 2H), 1.97-2.03 (m, 2H), 1.67-1.74 (m, 2H), 1.44-1.60 (m, 2H), 1.23-1.37 (m, 14H), 0.90 (t, J=6.8 Hz, 3H), 0.87 (t, J=7.0 Hz, 3H); $^{13}$C NMR (101 MHz, CDCl$_3$): δ 199.76, 176.29, 161.56, 131.20, 130.70 (2C), 114.81 (2C), 76.12, 38.56, 32.78, 32.03, 31.80, 29.53, 29.40, 29.36, 25.36, 24.51, 22.87, 22.76, 14.33, 14.20. The acid (468 mg, 1.3 mmol) was then converted to the sodium salt according to the procedure used for the preparation of Compound I to give Sodium (RS)-2-[4-Hexanoylphenoxy]decanoate (459 mg, 93%) as a white solid. mp 275-280° C.; $^1$H NMR (400 MHz, CD$_3$OD): δ 7.91 (d, J=8.8 Hz, 2H), 6.96 (d, J=8.8 Hz, 2H), 4.44-4.48 (m, 1H), 2.89-2.96 (m, 2H), 1.88-1.96 (m, 2H), 1.63-1.71 (m, 2H), 1.44-1.61 (m, 2H), 1.24-1.38 (m, 14H), 0.84-0.93 (m, 6H); $^{13}$C NMR (101 MHz, CD$_3$OD): δ 200.89, 177.86, 163.36, 130.27 (2C), 129.60, 114.75 (2C), 79.54, 37.94, 33.18, 31.86, 31.49, 29.44, 29.38, 29.21, 25.73, 24.55, 22.58, 22.45, 13.36, 13.23; LRMS (ESI): m/z 769.8 (M$_2$H$^+$), 747.8 (2M−Na$^+$+2H$^+$), 363.2 (M−Na$^+$+2H$^+$); HPLC: 3 .min.

Example 7

Sodium (RS)-4-Octanoylindane-2-carboxylate XXVI

Methyl (RS)-4-octanoyl-2-carboxylate (71 mg, 4%) was isolated as a side product during the preparation of its isomer, methyl (RS)-5-octanoyl-2-carboxylate. $^1$H NMR (400 MHz, CDCl$_3$): δ 7.66 (d, J=7.6 Hz, 1H), 7.35 (d, J=7.4 Hz, 1H), 7.24 (dd, J=7.6, 7.6 Hz, 1H), 3.69 (s, 3H), 3.64 (A of ABX, J=18.0, 9.4 Hz, 1H), 3.48 (B of ABX, J=18.1, 7.3 Hz, 1H), 3.13-3.34 (m, 3H), 2.90 (t, J=7.5 Hz, 2H), 1.68 (tt, J=7.2, 7.2 Hz, 2H), 1.24-1.38 (m, 8H), 0.86 (t, J=6.9 Hz, 3H); $^{13}$C NMR (101 MHz, CDCl$_3$): δ 203.01, 176.79, 144.82, 143.67, 134.73, 129.30, 128.35, 127.83, 52.91, 44.06, 40.82, 38.71, 36.44, 32.73, 30.34, 30.19, 25.36, 23.64, 15.10. The methyl ester (71.0 mg, 0.24 mmol) was saponified according to the standard protocol to give (RS)-4-octanoyl-2-carboxylic acid (66.0 mg, 96%) as an off-white solid. $^1$H NMR (400 MHz, CDCl$_3$): δ 7.69 (d, J=7.6 Hz, 1H), 7.39 (d, J=7.4 Hz, 1H), 7.26 (dd, J=7.6, 7.6 Hz, 1H), 3.67 (A of ABX, J=18.0, 9.0 Hz, 1H), 3.56 (B of ABX, J=18.0, 6.9 Hz, 1H), 3.19-3.39 (m, 3H), 2.93 (t, J=7.4 Hz, 2H), 1.70 (tt, J=7.3, 7.3 Hz, 2H), 1.24-1.38 (m, 8H), 0.88 (t, J=6.9 Hz, 3H). The resulting acid (66.0 mg, 0.23 mmol) was then converted to the sodium salt according to the standard protocol to give sodium (RS)-4-octanoyl-2-carboxylate (70.0 mg, 99%) as an off-white solid. mp 106-110° C.; $^1$H NMR (400 MHz, CD$_3$OD): δ 7.69 (d, J=7.8 Hz, 1H), 7.38 (d, J=7.4 Hz, 1H), 7.24 (dd, J=7.6, 7.6 Hz, 1H), 3.37-3.56 (m, 2H), 3.10-3.21 (m, 3H), 2.95 (t, J=7.3 Hz, 2H), 1.66 (tt, J=7.3, 7.3 Hz, 2H), 1.26-1.39 (m, 8H), 0.89 (t, J=6.8 Hz, 3H); $^{13}$C NMR (101 MHz, CD$_3$OD): δ 203.56, 182.93, 145.34, 143.96, 133.93, 128.26, 126.97, 126.42, 47.62, 39.89, 38.69, 36.70, 31.76, 29.21, 29.17, 24.55, 22.52, 13.28; LRMS (ESI): m/z 577 (2M−2Na$^+$+3H$^+$), 289 (M−Na$^+$+2H$^+$); HPLC: 3.0 min.

In general, all keto compounds of the present invention may be prepared by three different methods. The first route is a coupling reaction between an alkylketophenol and bromoalkyl ester in the presence of a base such as potassium carbonate. The next step is saponification of the ester followed by the formation of the metal salt. Also, modification of this procedure may be undertaken by use of a bromoalkyl acid instead of the ester. In this case, the potassium salt formed during the coupling reaction is neutralized in situ to the corresponding acid which is then converted to the desired metal salt. The second approach involves a Grignard reaction between alkyl magnesium bromide and aldehyde benzoate or aldehyde phenylacetate derivatives. The resulting alcohol is oxidized to the corresponding ketone followed by saponification of the ester to the acid and subsequent formation of the metal salt. The third route employs a Fiedel-Craft reaction between the acid chloride and aralkyl ester. This gives the ketoester which can be converted to the acid and then the final product metal salt.

Example 8

Effect of Compounds on IL-12 Production on LPS-stimulated RAW264.7 Cells

IL-12 is a key regulator of T helper (Th1/Th2) balance, which is critically skewed, one way or the other, in several infections; autoimmunity, atopy and tumors. Compounds increasing IL-12 production may be useful in the treatment of several diseases including but not limited to atopic and allergic conditions; I. J. Elenkov et al. in *Ann. NY Acad. Sci.* 917, 94-105 (2000), HIV infection; F. Villinger et al. in *European Cytokine Network* 21(3), 215-218 (2010), promotion of hematopoiesis; L. A. Basile et al. in *J. Translational Medicine* DOI 10.1186/1479-5876-6-26 (2007), and inhibition of fibrosis-related disease M. P. Keane et al. in *Am. J. Physiol. Lung Cell Mol. Physiol.* 281, L92-L97 (2001). As noted hereinabove, it has been demonstrated that IL-12 inhibits fibrocyte differentiation; D. D. Shao et al. in *J. Leukoc. Biol.* 83, 1323-1333 (2008). Fibrocytes are circulating mesenchymal progenitor cells that participate in tissue responses to injury and invasion. Accumulating knowledge from animal models regarding the differentiation, trafficking and function of these cells implicates them in the development of diseases characterized by chronic inflammation and excessive collagen deposition. These pathologic disorders and fibrotic diseases, for example, E. L. Herzog and R. Bucala in *Experimental Hematology* DOI 10.1016/j.exphem.2010.03.004 (2010), include asthma, pulmonary fibrosis (idiopathic pulmonary fibrosis; most common form of the disease), skin diseases (fibrocytes have been identified in the skin of patients with cutaneous fibrosing diseases such as scleroderma and nephrogenic systemic fibrosis); cardiac diseases (ischemia, cardiomyopathy: fibrocytes have been postulated to contribute to familial hypertrophic obstructive cardiomyopathy), liver fibrosis arising from liver injury (whether infectious, autoimmune or toxin-induced), renal fibrosis (including but not limited to chronic kidney disease and diabetic kidney disease) and other different fibrosing disorders such as but not limited to aging, for example, J. Xu et al. in *J. Gerontol. A Biol. Sci. Med. Sci.* 64, 731-739 (2009).

The effect of selected compounds on IL-12 production was undertaken in RAW264.7 (macrophage-like) cells. RAW264.7 cells were cultured with 100 ng/mL of LPS in presence or absence of compounds for 21 h in a humidified atmosphere of 95% air-5% carbon dioxide at 37° C. IL-12 concentration in the culture medium was measured using the IL-12 ELISA according to the manufacturer (BD Biosciences) recommendations.

Table 2 represents the effect of representative compounds on IL-12 production. All compounds induce a significant increase in IL-12 production under inflammatory conditions (i.e. in the presence of LPS). Compounds have no effect on IL-12 production in the absence of LPS.

TABLE 2

Effect of representative compounds on IL-12 production

| | IL-12 (pg/mL) |
|---|---|
| Control | ≤2 |
| LPS | ≤10 |
| Compound I (0.05 mM) | 209 |
| Compound II (0.5 mM) | 1099 |
| Compound III (0.05 mM) | 53 |
| Compound VIII (0.02 mM) | 12 |
| Compound IX (0.04 mM) | 73 |
| Compound X (0.02 mM) | 54 |
| Compound XXVI (0.1 mM) | 25 |

The effect of Compound I on IL-12 production under non-inflammatory and inflammatory conditions is shown in FIG. 1. Compound I increases IL-12 production in vitro (RAW.264 cells) only when inflammation is present.

These results demonstrate that compounds of Formula I and Formula II, in the presence of LPS, induce the production of IL-12. The ability to simulate the production of IL-12 means that compounds of the present invention may be useful for preventing and/or treating blood disorders (e.g., anemia, neutropenia), inflammation-related diseases and fibrosis related organ dysfunction as a result of the induction of IL-12. This is supported by the reference hereinabove, L. A. Basile et al. in *J. Translational Medicine* DOI 10.1186/1479-5876-6-26 (2007) which teaches that IL-12 stimulates hematopoiesis (white blood cells, red blood cells and platelets). This is further supported by T. K. Tarrant et al. in *J. Experimental Medicine* 189, 219-230 (1999) which teaches that the skewed T helper (Th1/Th2) balance in autoimmune disease may be favorably shifted to protect against further disease in work undertaken in a mouse model for experimental autoimmune uveitis, provided that treatment was undertaken within a specified time. The use of IL-12 for restoration of T helper cell balance in autoimmune disease is further illustrated by U.S. Pat. No. 7,534,430 (2009). This patent teaches the use of IL-12 and IL-12 antagonists for restoration of immune cell balance and treatment of multiple autoimmune diseases. Finally, this is still further supported by references described hereinabove which teach that IL-12 diminishes fibrosis by inhibition of the production of CTGF (at the molecular level, also see example 5) and inhibition of the differentiation of fibrocytes. Fibrosis is responsible for morbidity and mortality associated with organ dysfunction and subsequent organ failure.

Example 9

Effect of Compounds on TGF-β Induced CTGF Production on Normal Human Dermal Fibroblasts (NHDF)

Fibrosis refers to the excessive and persistent formation of scar tissue, which is responsible for morbidity and mortality associated with organ failure in a variety of chronic diseases affecting the lungs, kidneys, eyes, heart, liver, and skin (X. Shi-Wen, A. Leask, D. Abraham in *ScienceDirect* 19, 133-144 (2008). For example in kidney disease, regardless of disease etiology, tubulointerstitial fibrosis is a final common pathway in chronic kidney disease (CKD) that leads to disease progression and ultimately end stage renal disease (ESRD). CTGF has been implicated in this process through its effects on promoting epithelial to mesenchymal transition (EMT). EMT is a cellular process that transforms normal functioning cells into myofibroblast cells, which produce components of scar tissue. In the normal process of tissue repair, EMT promotes healing of tissues and is shut down once healing has occurred. However, recurring insult and injury, such as that which occurs in chronic disease, results in an imbalance of growth factors (elevated levels of CTGF) and dysfunctional signaling, leading to persistent EMT. CTGF drives EMT occurring in multiple types of tissues including kidney, lung, and liver. Recent studies also implicate CTGF in other pathologies associated with CKD including hyperfiltration, proteinuria, hypertrophy, and microvascular leakage. There is evidence that anti-CTGF therapy may provide some reversal of the disease process.

The effect of selected compounds on CTGF production was undertaken in NHDF. Cells were cultured in DMEM (0.5% FBS) with or without 10 ng/mL of TGF-β for 48 h in a humidified atmosphere of 95% air-5% carbon dioxide at 37° C. CTGF production in the culture medium was measured using the CTGF ELISA according to the manufacturer (Prepotech) recommendations. Table 3 represents the effect of selected representative compounds on the inhibition of TGF-βCTGF production in normal human dermal fibroblast (NHDF).

TABLE 3

Effect of representative compounds on the inhibition of TGF-induced CTGF production in NHDF

| | Concentration (µM) | CTGF inhibition (%) |
|---|---|---|
| Compound I | 7.5 | 41 |
| Compound II | 200 | 49 |
| Compound III | 62.5 | 45 |
| Compound XXVI | 100 | 59 |

These results demonstrate that compounds of Formula I and Formula II inhibit the production of CTGF. The ability to inhibit the production of CTGF means that compounds of the present invention may be useful for preventing and/or treating fibrosis and fibrosis-related organ dysfunction. This is supported by the important role of CTGF in the fibrotic process as described in this example hereinabove and elsewhere above (see Section D—fibrosis). This is further supported by the fact that it has been recently demonstrated that a human monoclonal antibody to CTGF reversed fibrosis in a model of radiation-induced lung fibrosis; press release from Fibrogen Inc., May 17, 2010, and presented at the International Conference of the American Thoracic Society in New Orleans, USA (abstract #A1054).

Example 10

In Vivo Effect of Compound I and Compound II on Renal Protection in Doxorubicin-induced Nephrotoxicity Model Demonstration of the in vivo protection by oral administration of Compound I and Compound II was undertaken in the doxorubicin-induced nephrotoxicity model using the following procedure. C57BL/6 mice (6 to 10 week old) were treated with compounds prophylacticly from day −3 to day 10. Nephrotoxicity was induced by an intravenous injection of 10 mg/kg of doxorubicin at day 0. Serum albumin was monitored at day 11.

Figure 2:
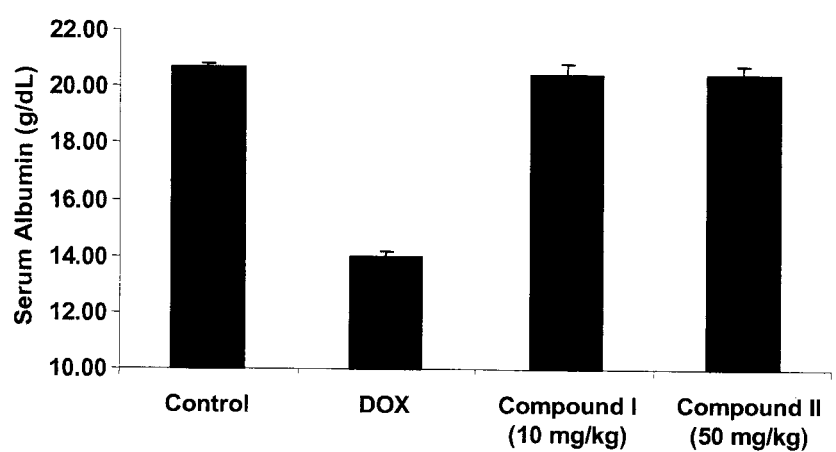
FIG. 2 is a bar graph showing in vivo effects of Compound I and Compound II on renal protection in the doxorubicin-induced nephrotoxicity mouse model.

As shown in FIG. 2, prophylactic treatment with Compound I or Compound II inhibits the decrease of serum albumin induced by doxorubicin.

Figure 3:
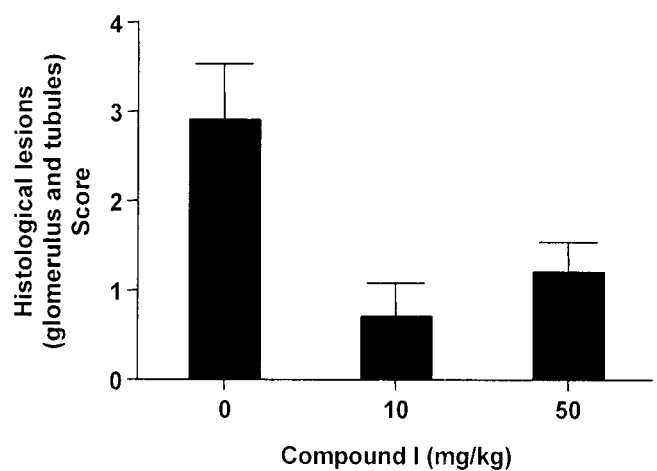
FIG. 3 is a bar graph showing that prophylactic treatment with Compound I reduces kidney lesions in mice induced by doxorubicin.

Doxorubicin is well known to induce nephro- and cardiotoxicity. FIG. 3 represents the histological kidney lesions score as determined by histochemistry in the doxorubicin-induced nephrotoxicity model. As shown in FIG. 3, doxorubicin induces significant kidney lesions at day 11. Prophylactic treatment with Compound I reduces the kidney lesions at the glomerular and tubular level induced by doxorubicin. Similar results were observed with Compound II.

Figure 4:
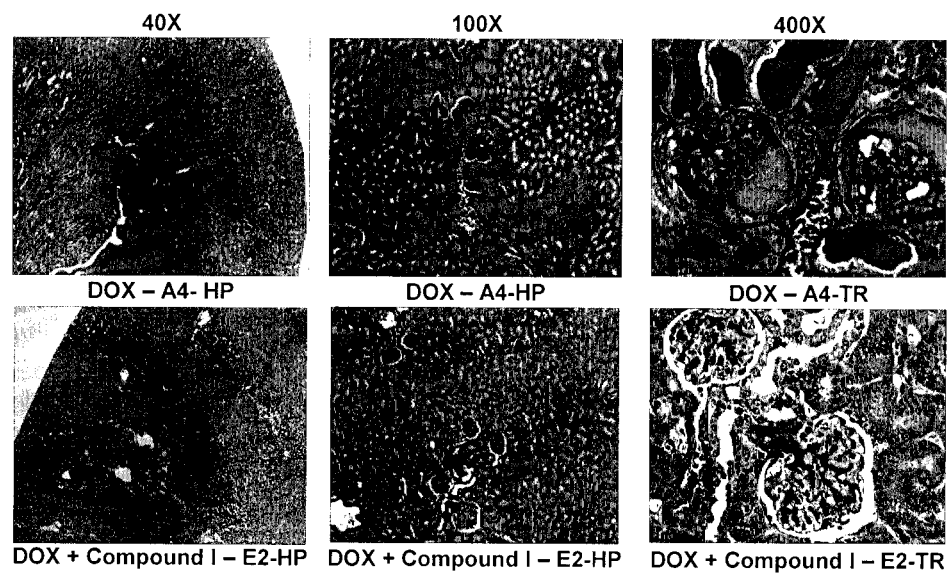
FIG. 4 represents histological micrographs of doxorubicin-induced lesions in control and Compound I-treated mice.

Doxorubicin induces early lesions primarily at the tubular region. Toxicity is further extended to the glomerulus (around day 11 post-doxorubicin). FIG. 4 displays the histological micrographs of doxorubicin-induced lesions in control and Compound I-treated mice. Doxorubicin induces kidney cell apoptosis, fibrosis, sclerosis and accumulation of proteins in affected tubular regions. Treatment with Compound I protects the kidney against doxorubicin toxicity.

Figure 5:
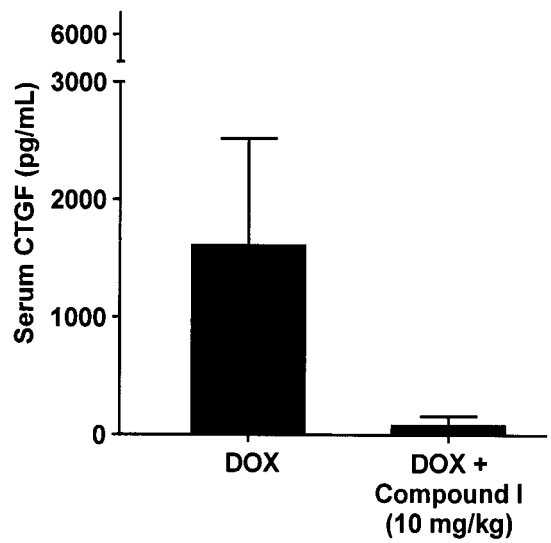
FIG. 5 is a bar graph showing effects of oral treatment with Compound I on serum CTGF in the doxorubicin-induced nephrotoxicity mouse model.

The mechanism by which Compound I appears to protect against doxorubicin-induced nephrotoxicity involves inhibition of fibrosis as demonstrated by the significant inhibition of CTGF production in serum of animals treated with Compound I. FIG. 5 illustrates that the effects of oral treatment with Compound I on serum CTGF in the doxorubicin-induced nephrotoxicity model. Doxorubicin induces a significant increase in serum CTGF which is prevented by treating with Compound I (p<0.01).

These results demonstrate that compounds of Formula I and Formula II inhibit the in vivo production of CTGF, relative to doxorubicin-treated mice, and subsequently diminish tissue damage resulting from fibrosis, as evidenced by the lesions score, tissue micrographs and normalization of the serum albumin concentration. The above provides in vivo evidence that the compounds of the present invention may be useful for preventing and/or treating drug-induced (doxorubicin) inflammation and subsequent fibrosis related organ dysfunction, especially in the case of the kidney.

Example 11

Chemoprotection Studies

Female C57BL/6 mice, 6 to 8 week old, were immunosuppressed by treatment with 250 mg/kg of cyclophosphamide administered intravenously at day 0. To examine the immunoprotective effect of Compound I and Compound II, mice were pre-treated orally at day −3, −2 and −1 with 50 mg/kg of each compound. Mice were sacrificed at day +5 by cardiac puncture and cervical dislocation. Then, a gross pathological observation of the femurs (as a source of bone marrow cells) was recorded. After the sacrifice, tissues were crushed in PBS buffer and cells were counted on a hemacytometer.

Figure 6:
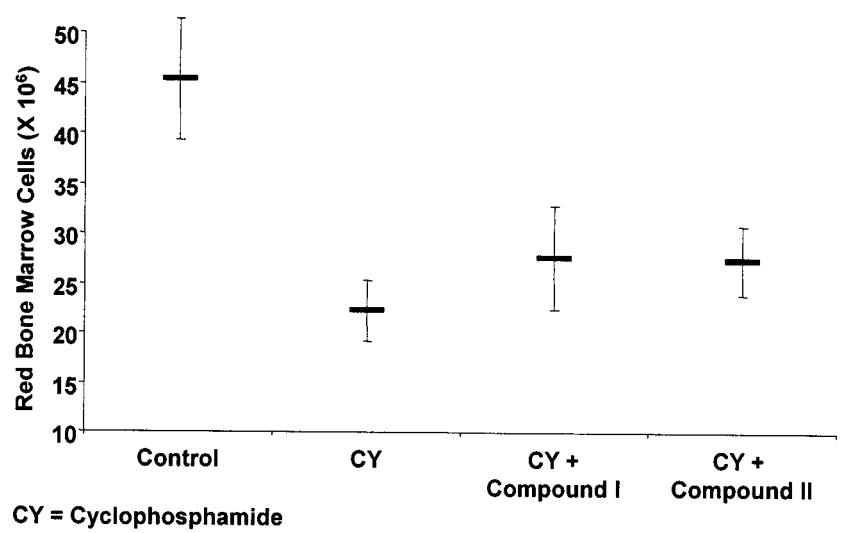
FIG. 6 is a graph showing a significant increase in red bone marrow cell count upon oral treatment with Compound I and Compound II in cyclophosphamide immunosuppressed mice.
Figure 7:
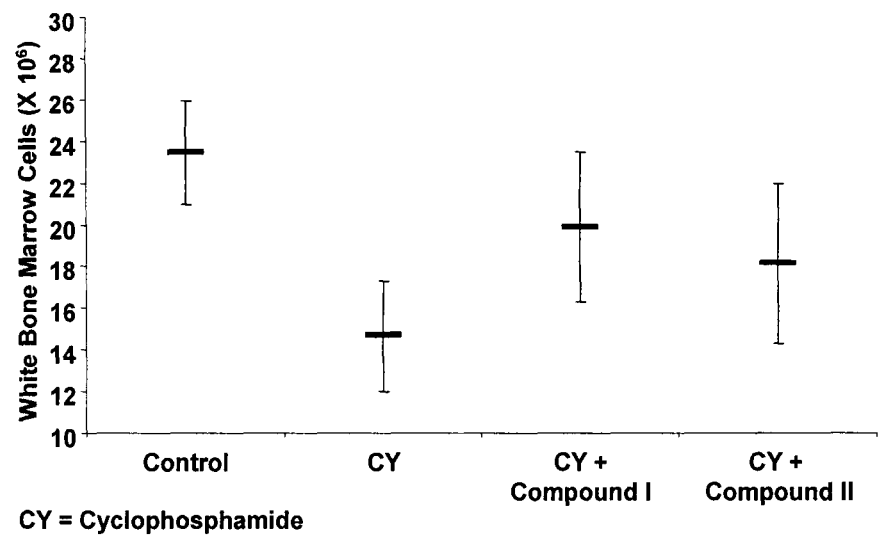
FIG. 7 is a graph showing a significant increase in white bone marrow cell count upon oral treatment with Compound I and Compound II in cyclophosphamide immunosuppressed mice.

A significant increase in red bone marrow cell count was observed with oral pre-treatment with Compound I and II in cyclophosphamide treated mice (FIG. 6). Furthermore, an increase in white bone marrow cell count was observed with oral pre-treatment with both compounds in cyclophosphamide immunosuppressed mice (FIG. 7).

Example 12

5/6-Nephrectomy as a Model of Kidney Fibrosis

Male 6-week old Wistar rats were subjected to 516-nephrectomy (5/6-NX) or sham operations. Under ketamine anesthesia (60 to 100 mg/kg, i.p.), two-thirds of the left kidney was removed on day 0 followed by the right total nephrectomy on day 7. Sham operated rats underwent exposition of the kidneys and removal of the perirenal fat. Animals that underwent the sham operation were given vehicle (saline) and were used as controls. 5/6-NX animals were treated by gastric gavage with the vehicle or Compound I administered daily at 10 and 50 mg/kg, respectively. Animals were treated from day 1 to 132 and were sacrificed at day 133. To evaluate renal function, creatinine clearance was measured at day 21 and every subsequent three weeks. Glomerular filtration rate (GFR) was then calculated. Serum urea, serum creatinine and kidney CTGF along with histological lesion score were also evaluated.

Figure 8:
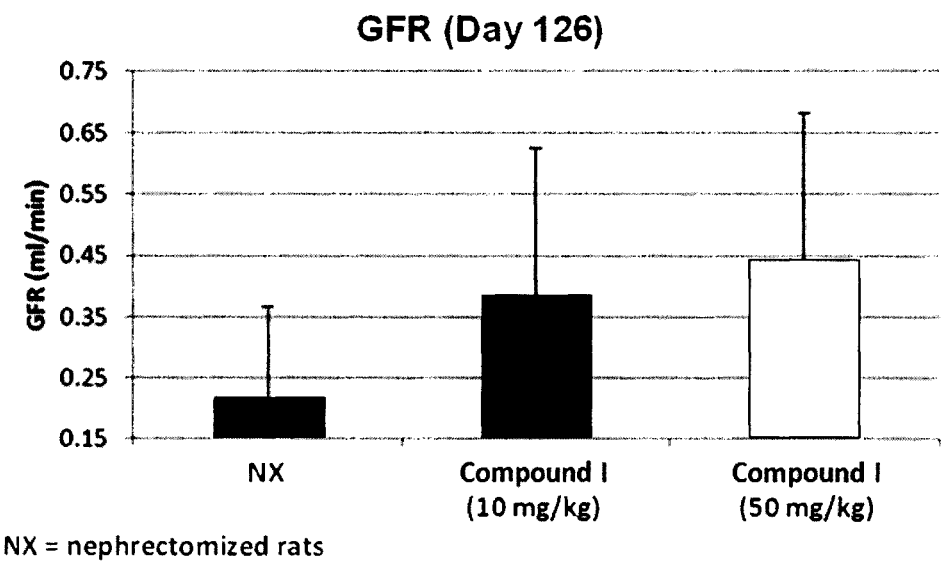
FIG. 8 is a bar graph showing the improvement in GFR obtained upon oral administration of Compound I in 5/6-nephrectomized (NX) rats.

Treatment with oral administration of Compound I resulted in an improvement of GFR at day 126 (p=0.08; FIG. 8).

Figure 9:
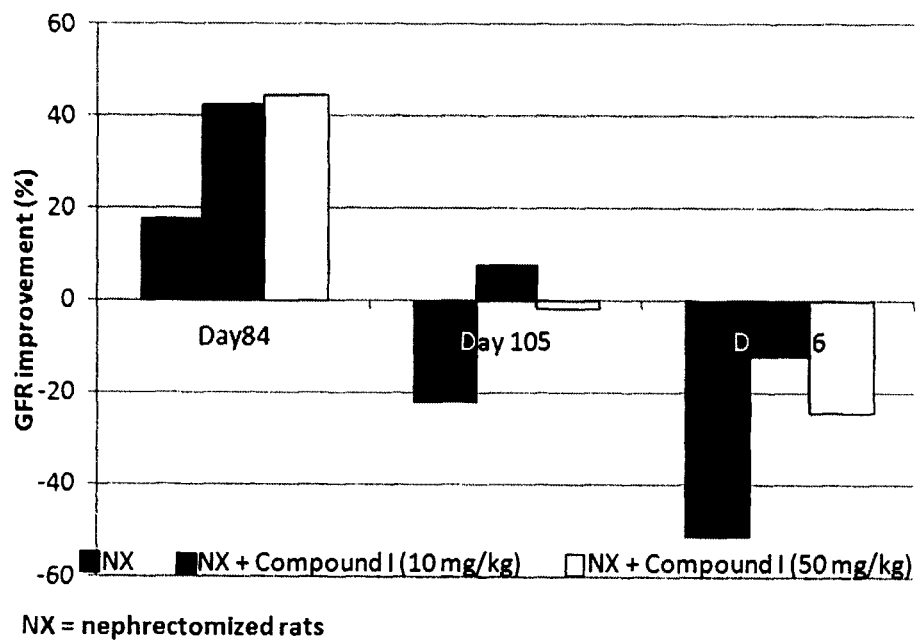
FIG. 9 is a bar graph showing the changes expressed in percent of GFR improvement, in 5/6-NX rats and 5/6-NX rats treated with Compound I (10 mg/kg and 50 mg/kg) at day 1 and day 125.

FIG. 9 illustrates the changes observed in GFR expressed as percent of improvement. While 5/6-NX rats showed a constant and gradual decrease of GFR from day 84 to day 126, animals treated with Compound I exhibited an improvement of GFR at day 84 and day 105. At day 126, the renal functions appeared to have deteriorated but to a lesser extent than that observed in the non-treated animals.

Figure 10:
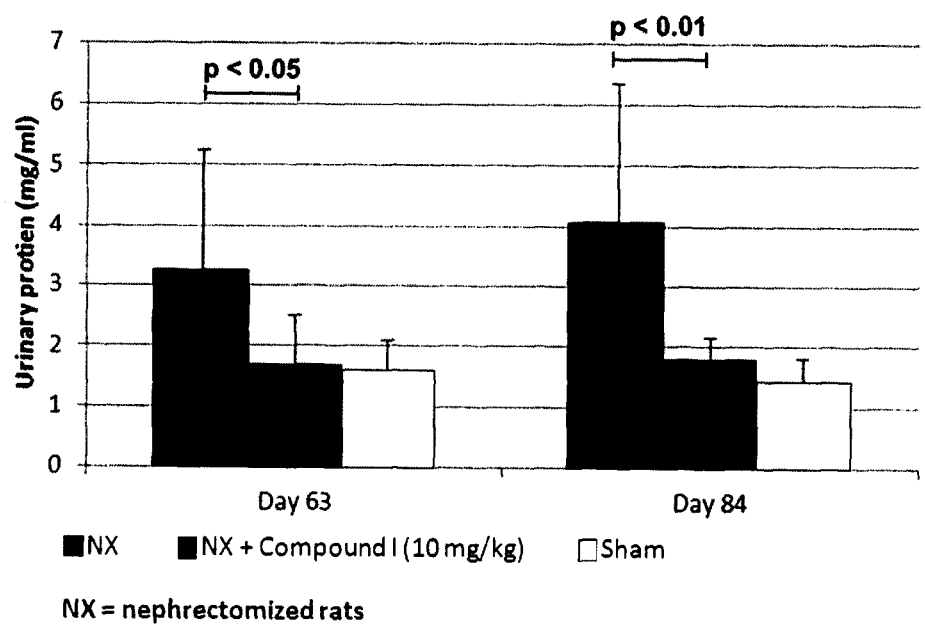
FIG. 10 is a bar graph showing that Compound I reduces proteinuria in 5/6-NX rats at a dose of 10 mg/kg at day 63 and day 84.

Furthermore, treatment with Compound I resulted in a reduction of proteinuria, as shown in FIG. 10.

Figure 11:
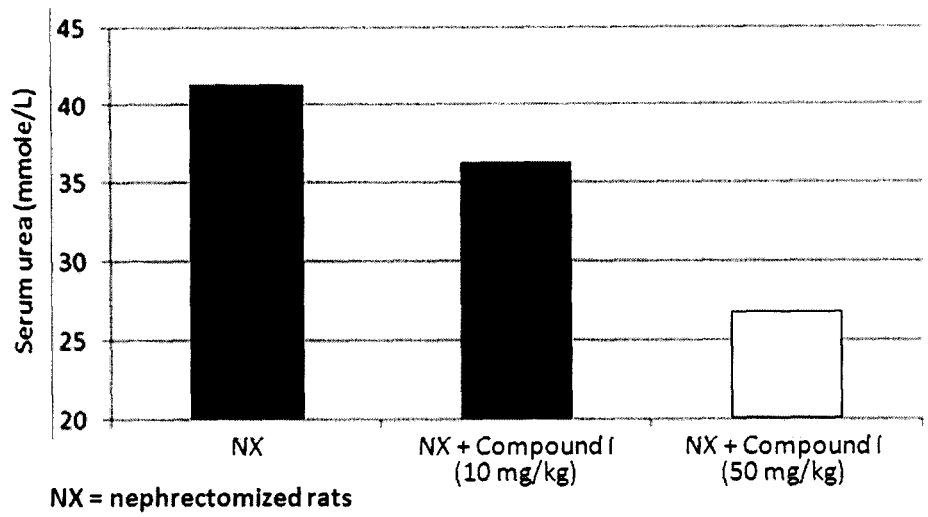
FIG. 11 is a bar graph showing that Compound I reduces serum urea in 5/6-NX rats when administered at a dose of 10 mg/kg and 50 mg/kg.

FIG. 11 illustrates that treatment of the animals with Compound I (10 and 50 mg/kg, oral administration) from day 1 to day 132 decreased serum urea.

Figure 12:
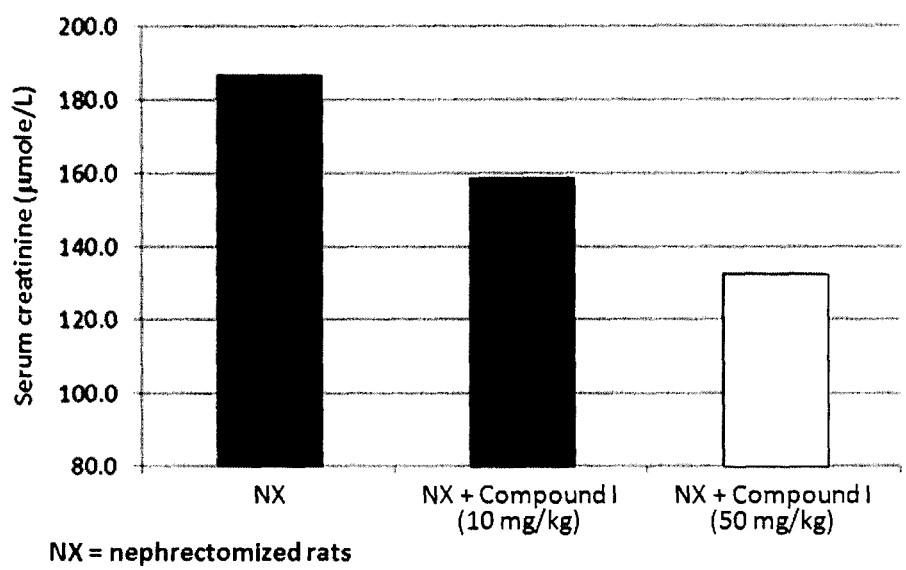
FIG. 12 is a bar graph showing the effect of Compound I on serum creatinine when administered at a dose of 10 mg/kg and 50 mg/kg.

FIG. 12 shows that Compound I treatment of 5/6-NX rats also decreased serum creatinine at day 126.

Figure 13:
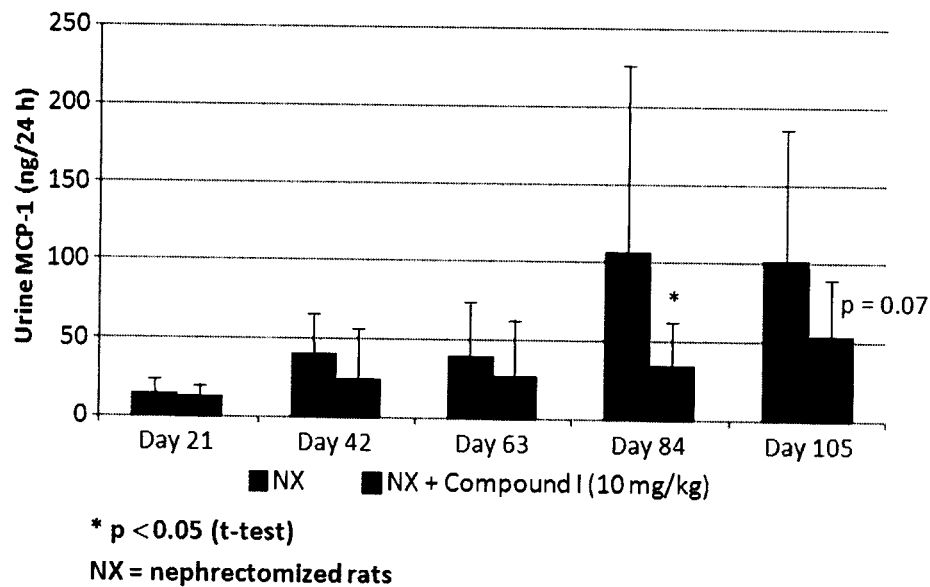
FIG. 13 is a bar graph showing the urinary excretion of MCP-1 in 5/6-NX rats and 5/6-NX rats treated with 10 mg/kg of Compound I at day 21, 42, 63, 84 and 105. Urinary excretion is significantly decreased (from day 84) in Compound I treated rats.

MCP-1 is a marker of the inflammatory state of the remnant kidney. FIG. 13 shows that excretion of urinary MCP-1 is markedly reduced in Compound I-treated 5/6-NX rats. This reduction correlates with GFR improvement and inhibition of inflammation and fibrosis observed in Compound I-treated rats.

Figure 14:
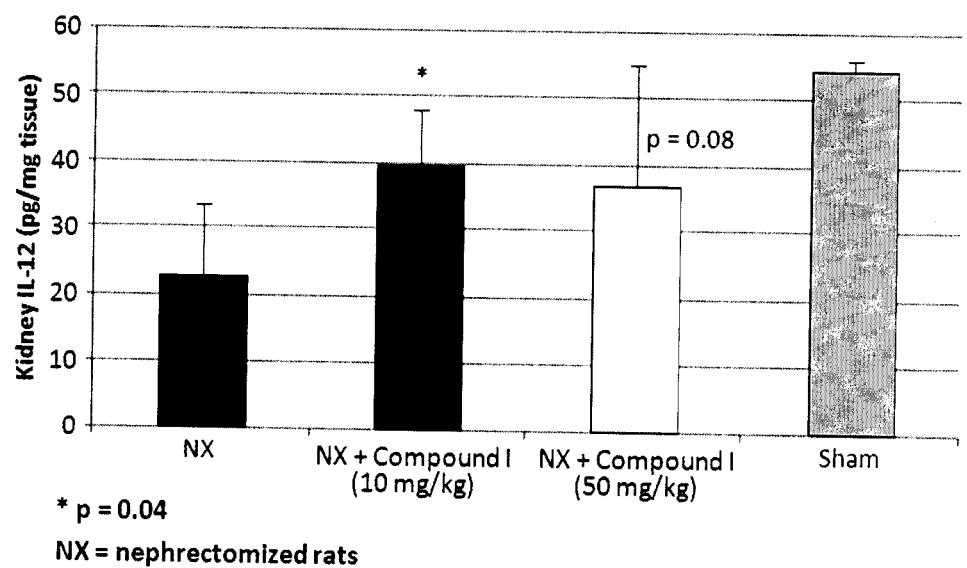
FIG. 14 is a bar graph showing the kidney IL-12p40 protein in 5/6-NX rats and 5/6-NX rats treated with 10 mg/kg or 50 mg/kg of Compound I. Kidney IL-12p40 is significantly increased in Compound I treated rats.

5/6-NX rats have a significant decrease in their kidney IL-12p40 level compared to sham. Oral treatment with Compound I induces a significant ($p=0.04$ at 10 mg/kg) increase in IL-12p40 which correlates with in vitro data. This increase is relative to the untreated 5/6-NX group and the IL-12p40 level is similar to that observed in the sham rats, as shown in FIG. 14.

Figure 15:
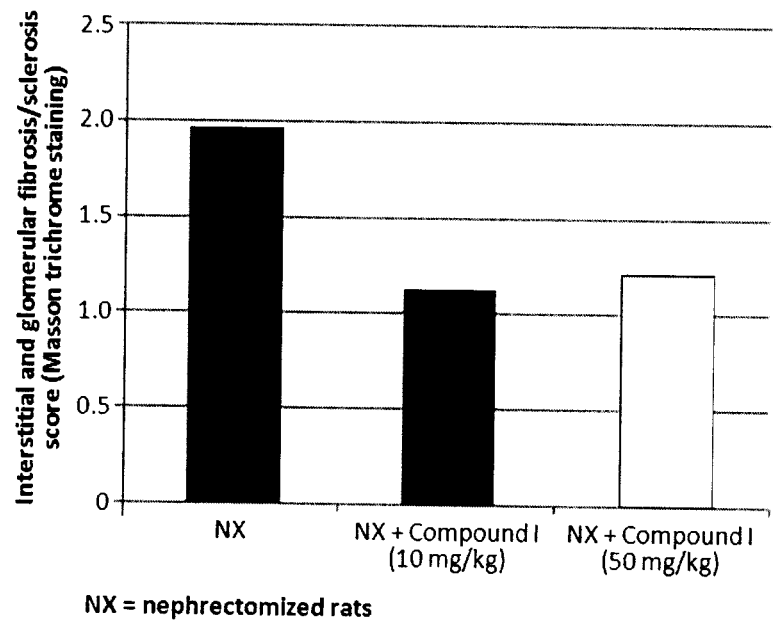
FIG. 15 is a bar graph showing the decrease in interstitial and glomerular fibrosis/sclerosis in treated 5/6-NX rats treated with 10 mg/kg or 50 mg/kg of Compound I.

Histological examination of the remaining renal tissue from these animals revealed significant differences between nephrectomized rats and nephrectomized rats treated with Compound I, as illustrated in FIG. 15. Kidney from Compound I-treated animals showed reduction of interstitial and glomerular fibrosis/sclerosis.

Figure 16:
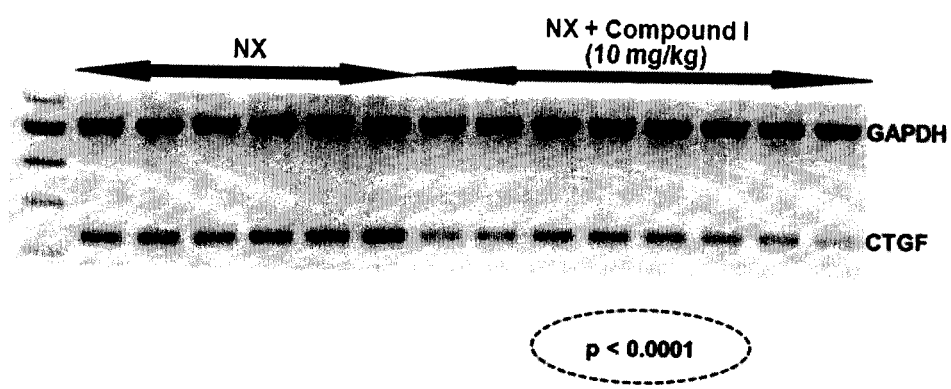
FIG. 16 is a Northern blot showing that the treatment of 5/6-NX rats with Compound I (oral, 10 mg/kg) reduces kidney CTGF expression in 5/6-NX rats.

Further analysis of the renal tissue revealed that the reduction of fibrosis was accompanied by a reduction of connective tissue growth factor (CTGF) expression in Compound I-treated rats, as illustrated in FIG. 16. This result corroborates with in vitro data.

CTGF, TGF-β, α-SMA (marker of myofibroblasts) and collagen 1 (marker of fibrosis) were quantified by real-time PCR. The results show that oral administration of Compound I (10 mg/kg) decreases significantly the expression of these markers in the remnant kidney.

Also, at an oral dose of 50 mg/kg of Compound I, nephrectomized rats did not require Ringer's lactate solution over the period of treatment.

Figure 17:
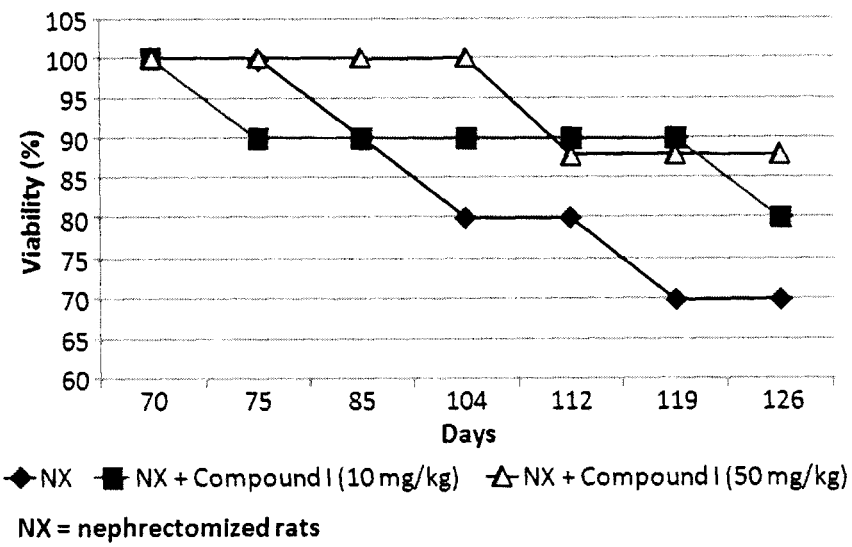
FIG. 17 is a graph showing the percentage of survival of 5/6-NX rats and 5/6-NX rats treated with oral administration of Compound I (oral, 10 mg/kg and 50 mg/kg). Treatment with Compound I increases the survival rate.

As shown in FIG. 17, Compound I increases the survival rate of 5/6-NX rats,

Example 13

Unilateral Ureteral Obstruction (UUO) Rat Model

The effect of treatment with Compound I was studied on the Unilateral Ureteral Obstruction (UUO) model, a model of kidney interstitial fibrosis. Sprague-Dawley rats were used at 6-8 weeks of age and 200-250 g in body weight. Rats were sedated by general anesthesia (isoflurane), then an incision was made in the left side of the back, and the left proximal ureter was exposed and triple-ligated. Sham-operated rats had their ureter exposed but not ligated. Rats were treated by oral gavage from day 1 to 13. Rats were sacrificed on day 14.

Figure 18:
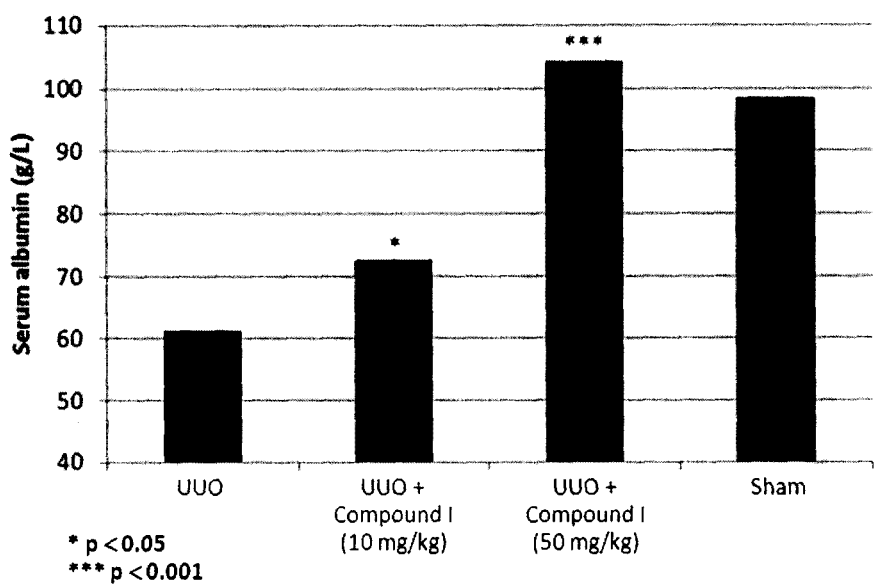
FIG. 18 is a bar graph showing the serum albumin concentration in UUO (Unilateral Ureteral Obstruction)-rats treated with Compound I (10 and 50 mg/kg).

Serum albumin loss was used as an indication of kidney injury. FIG. 18 illustrates that UUO induced a significant decrease of serum albumin which was prevented by oral administration of Compound I.

Figure 19:
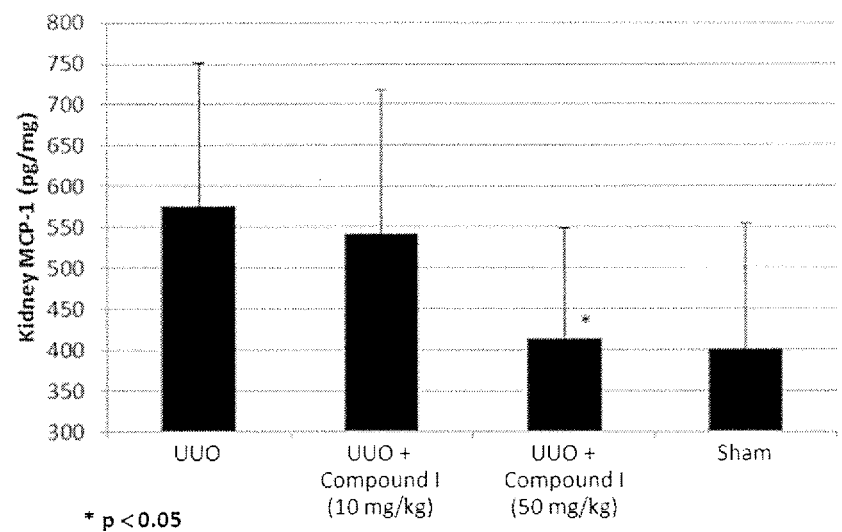
FIG. 19 is a bar graph showing the kidney MCP-1 level in UUO-rats treated with Compound I (10 and 50 mg/kg).

FIG. 19 shows that kidney MCP-1 is markedly increased in the ligated kidney which is indicative of inflammation and kidney MCP-1 is significantly reduced with 50 mg/kg treatment of Compound I in 5/6-NX rats.

Further analysis of the renal tissue revealed that oral treatment of Compound I reduced TGF-β expression in the kidney. A significant dose-response inhibition of the expression of CTGF and collagen 1 is also observed in animals treated with Compound I.

Overall, these results indicate a reduction of fibrosis as observed by an inhibition of TGF-β, CTGF and collagen 1 mRNA expression in the kidney.

Example 14

Epithelial to Mesenchymal Transition (EMT)

Evidence suggests that renal tubular epithelial cells can undergo epithelial to mesenchymal transition (EMT) to become matrix-producing fibroblasts under pathologic conditions. This phenotypic conversion not only illustrates the remarkable plasticity of mature, differentiated kidney epithelial cells, but is also fundamentally implicated in the pathogenesis of a wide range of chronic renal diseases. Recent studies provide compelling evidence that a large proportion of the interstitial fibroblasts in fibrotic kidneys originate from tubular epithelial cells via EMT. Likewise, selective blockade of tubular EMT, due to preservation of tubular basement membrane integrity in tPA−/− mice, protects the kidney from developing fibrotic lesions after obstructive injury. These observations underscore the crucial importance of tubular EMT in the onset and progression of chronic renal fibrosis that eventually results in end-stage renal failure. Several factors have been suggested as potential initiators of EMT in different in vitro and in vivo models. With the exception of CTGF, each of these mediators requires the induction of TGF-β to complete the process of EMT.

Figure 20:
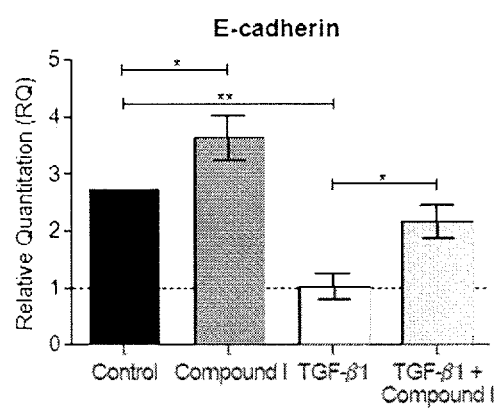
FIG. 20 is a bar graph showing the effect of Compound I on E cadherin in normal HK-2 cells and TGF-β induced EMT cells. Real-time PCR using human E-cadherin TagMan® Gene Expression Assay normalized to human GAPDH endogenous control; reference is TGF-β-treated cells 24h (RQ=1). * p<0.05, ** p<0.01 (t-test).
Figure 21:
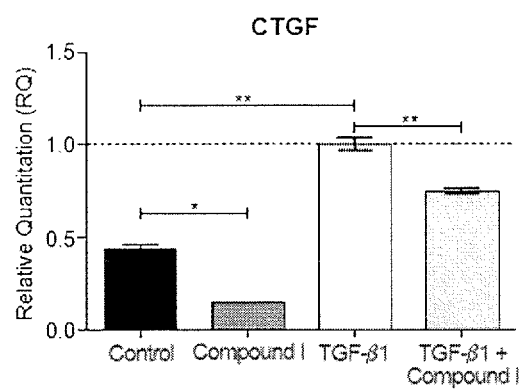
FIG. 21 is a bar graph showing the effect of Compound I on CTGF in normal HK-2 cells and TGF-β induced EMT cells. Real-time PCR using human CTGF TagMan® Gene Expression Assay normalized to human GAPDH endogenous control; reference is TGF-β-treated cells 24h (RQ=1). * p<0.05, ** p<0.01 (t-test).
Figure 22:
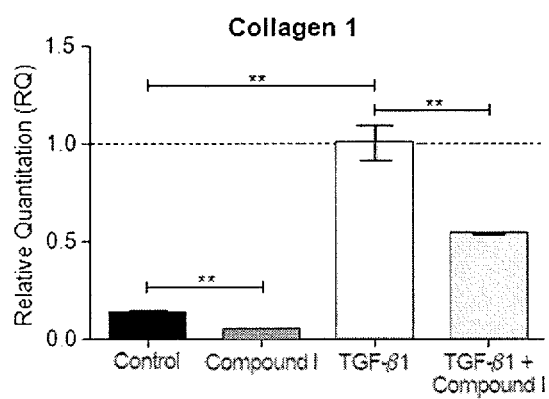
FIG. 22 is a bar graph showing the effect of Compound I on collagen 1 in normal HK-2 cells and TGF-p induced EMT cells. Real-time PCR using human Collagen 1 TaqMan® Gene Expression Assay normalized to human GAPDH endogenous control; reference is TGF-β-treated cells 24h (RQ=1). ** p<0.01 (t-test).

Further analysis was undertaken to determine the effect of Compound I on EMT. The effect of Compound I on TGF-β induced EMT was analyzed on human proximal tubule epithelial cells (HK-2). To assess the progression of EMT, the pro-epithelial marker E-cadherin and the mesenchymal/pro-fibrotic markers CTGF and collagen 1 were assayed by quantitative real-time PCR. To examine the prospective efficacy of Compound I in inhibiting TGF-β-induced EMT, we first verified the ability of TGF-β to induce EMT in HK-2 cells. As shown in FIGS. 20, 21 and 22, EMT was induced by TGF-β as determined by a downregulation of E-cadherin and upregulation of CTGF and collagen 1 transcript expression. Furthermore, TGF-β induced EMT was significantly inhibited by Compound I in both cells as demonstrated by an upregulation of E-cadherin and downregulation of CTGF and collagen 1. Furthermore, Compound I alone was able to downregulate basal expression of CTGF and collagen 1.

Headings are included herein for reference and to aid in locating certain sections These headings are not intended to limit the scope of the concepts described therein, and these concepts may have applicability in other sections throughout the entire specification Thus, the present invention is not intended to be limited to the embodiments shown herein but is to be accorded the widest scope consistent with the principles and novel features disclosed herein.

The singular forms "a", "an" and "the" include corresponding plural references unless the context clearly dictates otherwise.

Unless otherwise indicated, all numbers expressing quantities of ingredients, reaction conditions, concentrations, properties, and so forth used in the specification and claims are to be understood as being modified in all instances by the term "about". At the very least, each numerical parameter should at least be construed in light of the number of reported significant digits and by applying ordinary rounding techniques. Accordingly, unless indicated to the contrary, the numerical parameters set forth in the present specification and attached claims are approximations that may vary depending upon the properties sought to be obtained. Notwithstanding that the numerical ranges and parameters setting forth the broad scope of the embodiments are approximations, the numerical values set forth in the specific examples are reported as precisely as possible. Any numerical value, however, inherently contain certain errors resulting from variations in experiments, testing measurements, statistical analyses and such.

It is understood that the examples and embodiments described herein are for illustrative purposes only and that various modifications or changes in light thereof will be suggested to persons skilled in the art and are to be included within the present invention and scope of the appended claims.

The invention claimed is:

1. A compound of Formula I, or a pharmaceutically acceptable salt thereof, wherein the compound has the following structure:

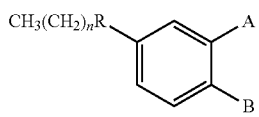

wherein:
n is 2-6;
R is —C(O)—, —OC(O)—, or —CH(OH)—;
A is

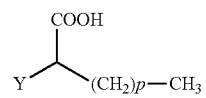

when B is H;
B is

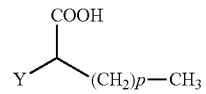

when A is H;
where:
Y is O, S, NH, or CH$_2$; and
p is 3-7.

2. The compound of claim 1, wherein R is —C(O)—.

3. The compound of claim 1, wherein the salt is a base addition salt.

4. The compound of claim 3, wherein the base addition salt comprises a metal counterion selected from sodium, potassium, magnesium, calcium and lithium.

5. The compound of claim 4, wherein the metal counterion is calcium.

6. A compound, or a pharmaceutically acceptable salt thereof, wherein the compound is any one of Compounds I, III-XIV and XVI:

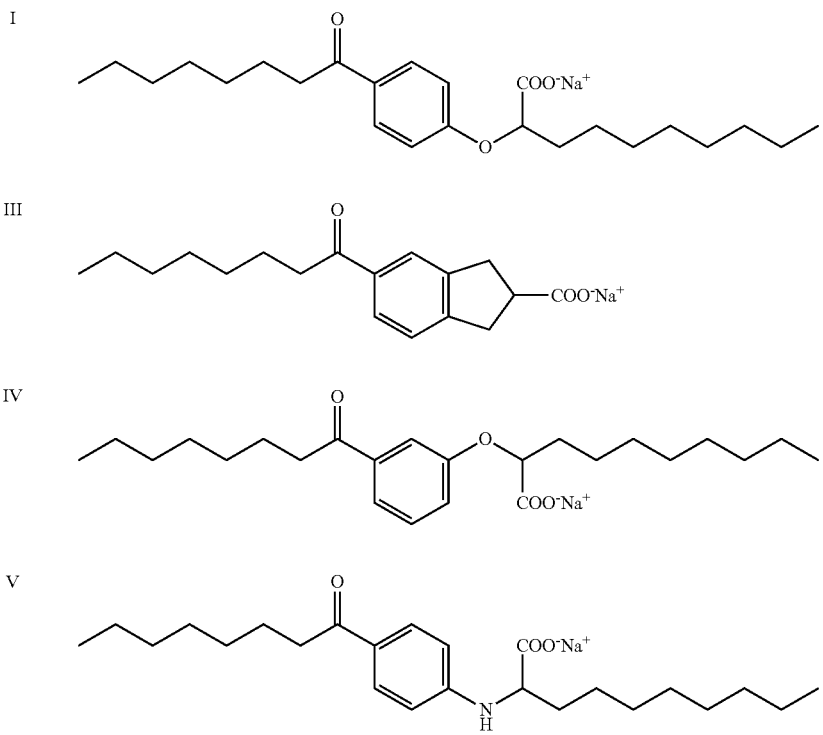

-continued
| Compound No. | Structure |
| --- | --- |
| VI | 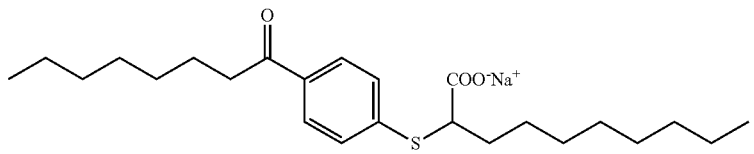 |
| VII | 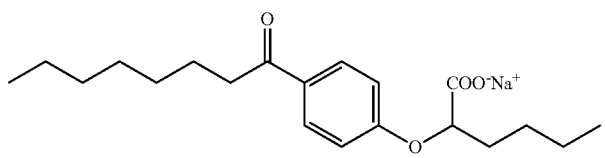 |
| VIII | 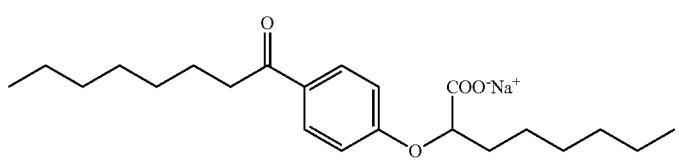 |
| IX | 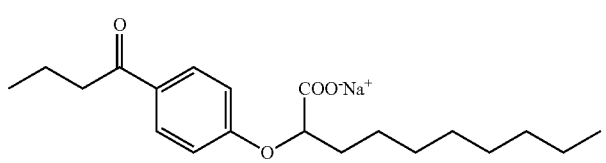 |
| X | 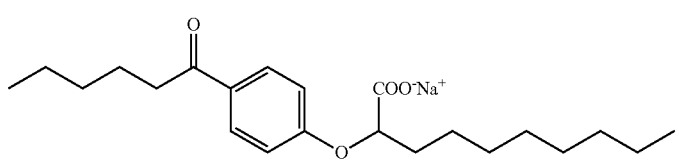 |
| XI | 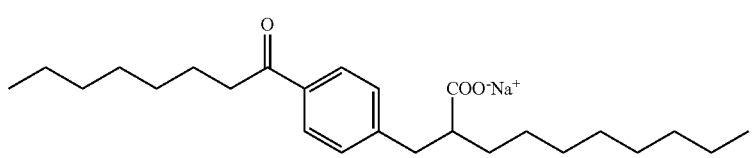 |
| XII | 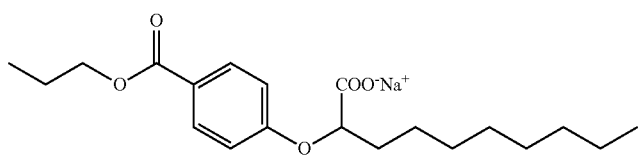 |
| XIII | 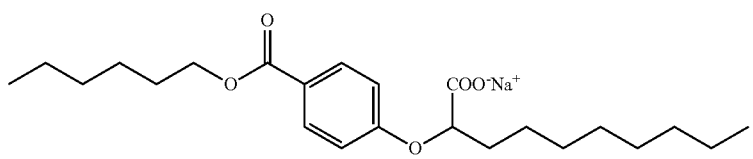 |
| XIV | 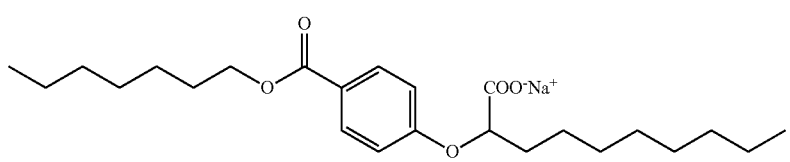 |

| Compound No. | Structure |
|---|---|
| XVI | 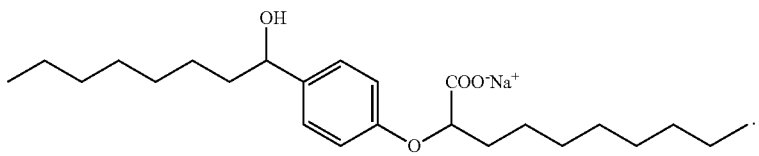 |

7. The compound of claim 6, wherein the compound is Compound I, III or X.

8. A pharmaceutical composition comprising a compound according to claim 1, and a pharmaceutically acceptable carrier.

9. A method for ameliorating: (i) anemia induced by chemotherapy, (ii) neutropenia induced by chemotherapy, (iii) a renal disorder or a renal disorder complication, or (iv) a fibrosis-related organ dysfunction wherein said method comprises administering, to a patient in need of such treatment, a compound of claim 1.

10. The method of claim 9, wherein the renal disorder is a nephropathy.

11. The method of claim 9, used for nephroprotection of a subject in need thereof against toxic effects arising from a treatment with a chemotherapeutic agent.

12. The method of claim 9, used for improving clearance of creatinine or clearance of uric acid.

13. The method of claim 9, wherein the fibrosis-related organ dysfunction is a fibrosis-related kidney dysfunction, a fibrosis-related heart dysfunction, a fibrosis-related lung dysfunction, a fibrosis-related liver dysfunction, nephropathy or a fibrosis-related brain dysfunction.

14. A compound of Formula I, or a pharmaceutically acceptable salt thereof, wherein the compound has the following structure:

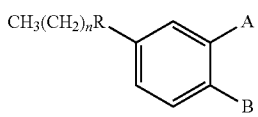

wherein:
n is 2-6;
R is —C(O)—, —OC(O)—, or —CH(OH)—;
A is

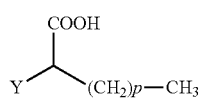

when B is H;
B is

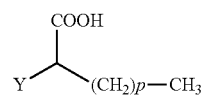

when A is H; or
A and B are covalently bonded to form a six (6) or seven (7)-membered cycloalkyl substituted with COOH;
where:
Y is O, S, NH, or CH$_2$; and
p is 3-7.

15. The compound of claim 14, wherein R is —C(O)—.

16. The compound of claim 14, wherein the salt is a base addition salt.

17. The compound of claim 16, wherein the base addition salt comprises a metal counterion selected from sodium, potassium, magnesium, calcium, and lithium.

18. The compound of claim 17, wherein the metal counterion is calcium.

19. A pharmaceutical composition comprising a compound according to claim 14, and a pharmaceutically acceptable carrier.

20. A method for ameliorating: (i) anemia induced by chemotherapy, (ii) neutropenia induced by chemotherapy, (iii) a renal disorder or a renal disorder complication, or (iv) a fibrosis-related organ dysfunction wherein said method comprises administering, to a patient in need of such treatment, a compound of claim 14.

21. The method of claim 20, wherein the renal disorder is a nephropathy.

22. The method of claim 20, used for nephroprotection of a subject in need thereof against toxic effects arising from a treatment with a chemotherapeutic agent.

23. The method of claim 20, used for improving clearance of creatinine or clearance of uric acid.

24. The method of claim 20, wherein the fibrosis-related organ dysfunction is a fibrosis-related kidney dysfunction, a fibrosis-related heart dysfunction, a fibrosis-related lung dysfunction, a fibrosis-related liver dysfunction, nephropathy or a fibrosis-related brain dysfunction.

* * * * *

UNITED STATES PATENT AND TRADEMARK OFFICE
CERTIFICATE OF CORRECTION

PATENT NO.         : 9,475,750 B2                                           Page 1 of 1
APPLICATION NO.    : 13/882363
DATED              : October 25, 2016
INVENTOR(S)        : Boulos Zacharie et al.

It is certified that error appears in the above-identified patent and that said Letters Patent is hereby corrected as shown below:

In the Specification

Column 5,
Line 15, "and TGF-p" should read -- and TGF-β --.

Column 23,
Line 34, "diluent" or" should read -- diluent or --.

Column 36,
Line 57, "Compound Ito" should read -- Compound I to --.

Column 37,
Line 36, "Compound Ito" should read -- Compound I to --.

Column 42,
Line 45, "to 516" should read -- to 5/6 --.

Column 43,
Line 44, "-NX rats," should read -- NX rats. --.

Signed and Sealed this
Twenty-fifth Day of April, 2017

Michelle K. Lee
*Director of the United States Patent and Trademark Office*